(12) United States Patent
Hao et al.

(10) Patent No.: US 11,046,701 B2
(45) Date of Patent: Jun. 29, 2021

(54) SALT OF CETAGLIPTIN, PREPARATION METHOD THEREOF, PHARMACEUTICAL COMPOSITION, AND USE THEREOF

(71) Applicant: CGENETECH (SUZHOU, CHINA) CO., LTD., Suzhou (CN)

(72) Inventors: Yan Hao, Suzhou (CN); Renyan Zhang, Suzhou (CN); Huiping Pan, Suzhou (CN); Fuzhi Zhang, Suzhou (CN); Shijie Yin, Suzhou (CN); Juping Ding, Suzhou (CN); Qiang Yu, Suzhou (CN)

(73) Assignee: CGENETECH (SUZHOU, CHINA) CO., LTD., Suzhou (CN)

( * ) Notice: Subject to any disclaimer, the term of this patent is extended or adjusted under 35 U.S.C. 154(b) by 0 days.

(21) Appl. No.: 16/626,220

(22) PCT Filed: May 29, 2018

(86) PCT No.: PCT/CN2018/088888
§ 371 (c)(1),
(2) Date: Dec. 23, 2019

(87) PCT Pub. No.: WO2019/205224
PCT Pub. Date: Oct. 31, 2019

(65) Prior Publication Data
US 2020/0123164 A1    Apr. 23, 2020

(30) Foreign Application Priority Data
Apr. 26, 2018  (CN) .......................... 201810384349.8

(51) Int. Cl.
C07D 487/04    (2006.01)
A61P 3/10    (2006.01)

(52) U.S. Cl.
CPC .............. *C07D 487/04* (2013.01); *A61P 3/10* (2018.01); *C07B 2200/13* (2013.01)

(58) Field of Classification Search
CPC .................................................. C07D 487/04
See application file for complete search history.

(56) References Cited

FOREIGN PATENT DOCUMENTS

| CN | 103351391 | * | 10/2013 |
|----|-----------|---|---------|
| CN | 103351391 A | | 10/2013 |

OTHER PUBLICATIONS

International Search Report issued in corresponding International Application No. PCT/CN2018/088888, dated Jan. 28, 2019, State Intellectual Property Office of the P.R. China, Beijing, China.
"A polymorphism and crystallisation of medicines and Crystallisation", Marzen Planetary Co., Ltd., pp. 56 to 102, and 304 to 317, 2002.
Yoshinaki, Hirayama, "organic compound crystal production handbook", Marzen Co. Japan; pp. 17 to 23, 37 to 40, 45 to 51, 57 to 65, 2008.
Notice of Reasons for Refusal issued in corresponding Japanese Patent Application No. 2020-522769; dated Nov. 10, 2020; 5 pgs.

* cited by examiner

*Primary Examiner* — Paul V Ward
(74) *Attorney, Agent, or Firm* — Hauptman Ham, LLP

(57) ABSTRACT

The present invention relates to a salt of a compound of formula (I),

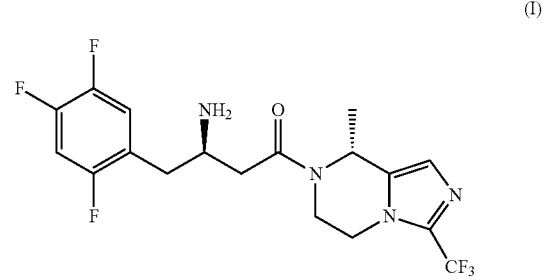

(I)

The salt is crystalline or amorphous phosphate, or crystalline or amorphous oxalate. Particularly, a crystal form B of the phosphate of the present invention has high crystallinity, low hygroscopicity and good stability, and the crystal form B of the phosphate is good in oral bioavailability, good in tolerance after long-term administration, difficult to induce hypoglycemia and good in inhibition effect on serum DPPIV.

12 Claims, 23 Drawing Sheets

| D-H···A | d(D···A)/Å | D-H···A | d(D···A)/Å |
|---|---|---|---|
| O6'-H6'A···O5 | 2.92 (4) | N1-H1C···F1 | 3.182(12) |
| N1-H1A···O5 | 2.699(18) | O2-H2···O1 | 2.708(10) |
| N1-H1B···O3 | 2.944(16) | | |

**, p<0.01 vs the model control group

SALT OF CETAGLIPTIN, PREPARATION METHOD THEREOF, PHARMACEUTICAL COMPOSITION, AND USE THEREOF

CROSS REFERENCE TO RELATED APPLICATIONS

The present application is a National Phase of International Application Number PCT/CN2018/088888, filed May 29, 2018, and claims the priority of Chinese Patent Application No. CN201810384349.8 filed on Apr. 26, 2018, the disclosure of which is incorporated herein by reference on its entirety.

TECHNICAL FIELD

The present invention relates to the field of chemical medicine, and more particularly to salt of cetagliptin, and preparation method, pharmaceutical composition, and use thereof.

BACKGROUND OF THE INVENTION

Cetagliptin, of which chemical name is (8R)-7-[(3R)-3-amino-1-oxo-4-(2,4,5-trifluorophenyl)butyl]-5,6,7,8-tetrahydro-8-methyl-3-(trifluoromethyl)imidazo[1,5-a]pyrazine, has the following structural formula (I):

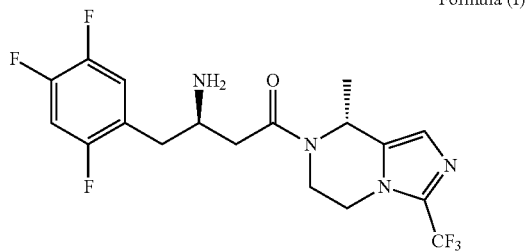

Formula (I)

The method for preparing cetagliptin refers to Example 1 in CN103351391B. Cetagliptin is a therapeutic drug for treating or preventing diseases related to dipeptidyl peptidase, for example, diabetes, especially type II diabetes.

At present, cetagliptin in the form of free base is viscous oil with poor druggability, and there have been no reports on salts or crystal forms of cetagliptin. Therefore, it is of great significance to develop salts of cetagliptin and study their crystal forms.

SUMMARY OF THE INVENTION

In the present invention, it was found by systematic screening that certain salts of cetagliptin have unexpected effects, are particularly suitable for processing preparations and have good pharmaceutical effect, low toxic and side effect and important drug development value.

The present invention aims to provide a salt of the compound of formula (I) suitable for drug research and industrial production, including phosphate and oxalate, wherein the provided phosphate is in a amorphous or crystal form, furthermore has two crystal forms, and the crystal forms of the phosphate in the present disclosure are named phosphate crystal form A and phosphate crystal form B, respectively; the provided oxalate is also in a amorphous or crystal form, and the crystal form of the oxalate in the present disclosure is named oxalate crystal form A.

To achieve the above objective, the present disclosure provides the following technical solutions.

An objective of the present disclosure is to provide a salt of the compound of formula (I),

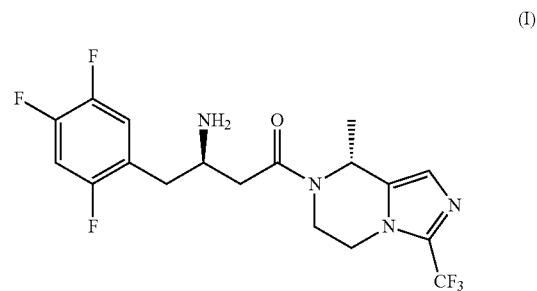 [SMILES: C[C@@H]1c2cnc(C(F)(F)F)n2CCN1C(=O)C[C@H](N)Cc1cc(F)c(F)cc1F]

(I)

The salt is crystalline or amorphous phosphate, or crystalline or amorphous oxalate.

Further, in the salt of the compound of formula (I), the molar ratio of the compound of formula (I) to an acid is 1:1.

For the amorphous form of the phosphate provided by the present disclosure, its X-ray powder diffraction pattern is substantially the same as FIG. 1.

For the amorphous form of the phosphate provided by the present disclosure, it has a weight loss of about 7.0% when heated to 150° C., and its thermogravimetric analysis chart is substantially shown in FIG. 2.

For the amorphous form of the phosphate provided by the present disclosure, it has a glass transition temperature of 47.6° C. (intermediate point temperature), and its differential scanning calorimetry analysis chart is substantially shown in FIG. 2.

Further, the salt is phosphate and in a form of crystal form A, and its X-ray powder diffraction pattern has characteristic peaks at positions of which the 2theta value is 15.8°±0.2°, 17.5°±0.2°, 19.1°±0.2° and 23.3°±0.2°.

Furthermore, its X-ray powder diffraction pattern has characteristic peaks at positions of which the 2theta value is 15.2°±0.2°, 20.1°±0.2° and 24.5°±0.2°.

Furthermore, its X-ray powder diffraction pattern has characteristic peaks at positions of which the 2theta value is 7.6°±0.2°, 22.8°±0.2° and 26.8°±0.2°.

In accordance with a specific and preferred aspect, its X-ray powder diffraction pattern is substantially the same as FIG. 4.

For the crystal form A of the phosphate provided by the present disclosure, it has a weight loss of about 6.4% when heated to 150° C., and its thermogravimetric analysis chart is substantially shown in FIG. 5.

For the crystal form A of the phosphate provided by the present disclosure, it has two endothermic peaks of 100.9° C. and 132.7° C. (peak temperature) before decomposition, respectively, and its differential scanning calorimetry analysis chart is substantially shown in FIG. 5.

Further, the salt is phosphate and in a form of crystal form B, and its X-ray powder diffraction pattern has characteristic peaks at positions of which 2theta value is 15.2°±0.2°, 15.9°±0.2°, 19.2°±0.2° and 23.3°±0.2°.

Furthermore, its X-ray powder diffraction pattern has characteristic peaks at positions of which the 2theta value is 22.9°±0.2°, 23.1°±0.2° and 26.9°±0.2°.

Furthermore, its X-ray powder diffraction pattern has characteristic peaks at positions of which the 2theta value is 20.2°±0.2°, 20.9°±0.2° and 24.6°±0.2°.

In accordance with a specific and preferred aspect, its X-ray powder diffraction pattern is substantially the same as FIG. 7.

For the crystal form B of the phosphate provided by the present disclosure, it has a weight loss of about 6.1% when heated to 150° C., and its thermogravimetric analysis chart is substantially shown in FIG. 8.

For the crystal form B of the phosphate provided by the present disclosure, it has two endothermic peaks of 103.2° C. and 133.5° C. (peak temperature) before decomposition, respectively, and its differential scanning calorimetry analysis chart is substantially shown in FIG. 8.

Further, the crystal form B is monohydrate.

Further, the salt is oxalate and in a form of crystal form A, and its X-ray powder diffraction pattern has characteristic peaks at positions of which the 2theta value is 9.8°±0.2°, 17.3°±0.2° and 24.9°±0.2°.

Furthermore, its X-ray powder diffraction pattern has characteristic peaks at positions of which the 2theta value is 16.7°±0.2°, 27.0°±0.2° and 29.5°±0.2°.

Furthermore, its X-ray powder diffraction chart has characteristic peaks at positions of which the 2theta value is 20.5°±0.2°, 21.3°±0.2° and 25.3°±0.2°.

In accordance with a specific and preferred aspect, its X-ray powder diffraction pattern is substantially the same as FIG. 26.

For the crystal form A of the oxalate provided by the present disclosure, it has a weight loss of about 7.6% when heated to 130° C., and its thermogravimetric analysis chart is substantially shown in FIG. 27.

For the crystal form A of the oxalate provided by the present disclosure, it has an endothermic peak of 121.3° C. (peak temperature) before decomposition, and its differential scanning calorimetry analysis chart is substantially shown in FIG. 27.

A second objective of the present disclosure is to provide a method for preparing a salt of the compound of formula (I), wherein the compound of formula (I) reacts with phosphoric acid in the presence of methyl tert-butyl ether, and precipitation with stirring or solvent evaporation is performed to obtain amorphous phosphate of the compound of formula (I).

A third objective of the present disclosure is to provide a method for preparing a salt of the compound of formula (I), wherein amorphous phosphate of the compound of formula (I) is dissolved in a mixed solvent of isoamyl alcohol and water, and solvent evaporation is performed to obtain the crystal form A.

Preferably, the volume ratio of the isoamyl alcohol to the water in the mixed solvent is 18-20:1.

Preferably, the amorphous phosphate of the compound of formula (I) is prepared by the following method: wherein the compound of formula (I) reacts with phosphoric acid in the presence of methyl tert-butyl ether, and precipitation with stirring or solvent evaporation is performed.

A fourth objective of the present disclosure is to provide a method for preparing a salt of the compound of formula (I), wherein amorphous phosphate of the compound of formula (I) is dissolved in ethanol, isopropyl alcohol or isoamyl alcohol, and solvent evaporation is performed to obtain a crystal form B; or, the amorphous phosphate of the compound of formula (I) is dissolved in a mixed solvent of isoamyl alcohol and water or a mixed solvent of isopropyl alcohol and methyl tert-butyl ether, and a crystal seed of the crystal form B is added for induced crystallization to obtain the crystal form B.

Preferably, the solvent evaporation is performed at 20° C.~30° C.

Preferably, the volume ratio of the isoamyl alcohol to the water in the mixed solvent is 18-20:1; the volume ratio of the isopropyl alcohol to the methyl tert-butyl ether in the mixed solvent is 0.8-1.2:1.

Preferably the amorphous phosphate of the compound of formula (I) is prepared by the following method, wherein the compound of formula (I) reacts with phosphoric acid in the presence of methyl tert-butyl ether, and precipitation with stirring or solvent evaporation is performed.

A fifth objective of the present disclosure is to provide a method for preparing a salt of the compound of formula (I), wherein the compound of formula (I) reacts with oxalic acid in the presence of methyl tert-butyl ether, and precipitation with stirring or solvent evaporation is performed to obtain amorphous oxalate of the compound of formula (I).

A sixth objective of the present disclosure is to provide a method for preparing a salt of the compound of formula (I), wherein the compound of formula (I) reacts with oxalic acid in the presence of methanol, and precipitation with stirring or solvent evaporation is performed to obtain the crystal form A.

A seventh objective of the present disclosure is to provide a pharmaceutical composition, including an active component and a pharmaceutically acceptable carrier, wherein the active component is the salt of the compound of formula (I).

An eighth objective of the present disclosure is to provide a use of the salt of the compound of formula (I) in preparation of a medicament for inhibiting the activity of dipeptidyl peptidase.

A ninth objective of the present disclosure is to provide a use of the salt of the compound of formula (I) in preparation of medicament for treating, controlling or preventing type II diabetes of mammals.

A tenth objective of the present disclosure is to provide a use of the salt of the compound of formula (I) in preparation of medicament for treating, controlling or preventing hyperglycemia of mammals.

Due to the implementations of the above technical solutions, the present disclosure has the following advantages, compared with the prior art.

The inventor of the present disclosure has screened and studied the formed salts of the compound of formula (I) and has found a new salt type suitable for drug development, so that the solubility of drugs is improved.

Particularly, the crystal form B of the phosphate of the present disclosure has high crystallinity, low hygroscopicity and good stability, and the crystal form B of the phosphate is good in oral bioavailability, good in tolerance after long-term administration, difficult to induce hypoglycemia and good in inhibition effect on serum DPPIV, thereby providing a better choice for the subsequent development of drugs.

DETAILED DESCRIPTION OF THE INVENTION

Figure 1:
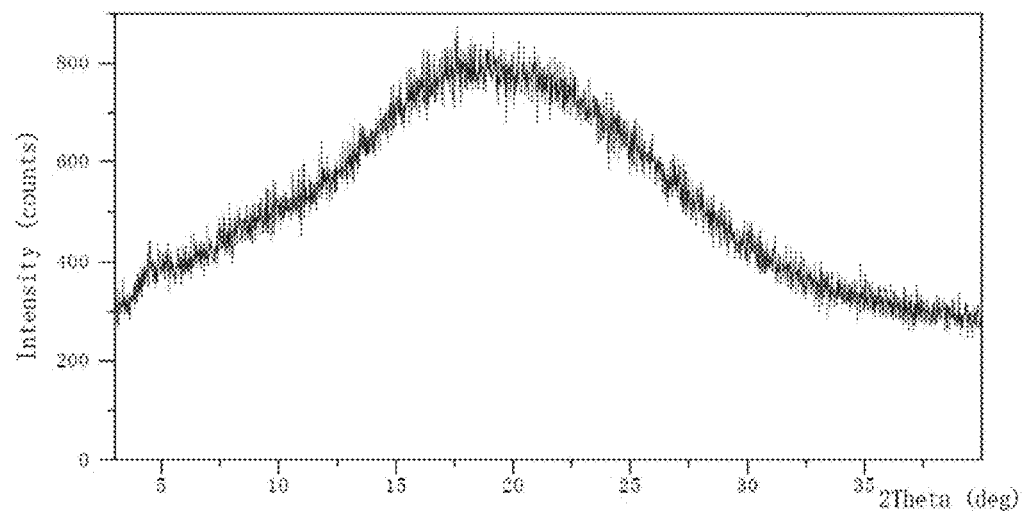
FIG. 1 shows an XRPD pattern of amorphous phosphate in Example 1.

The present invention will be further described below by specific examples, but it is not intented to limit the protection scope of the present invention. Those skilled in the art can make improvements to the preparation method and the used instruments within the scope of the claims, and those improvements shall also be regarded as falling into the protection scope of the present invention. Therefore, the protection scope of the present invention shall be subject to the appended claims.

The ratios not described in the present disclosure are volume ratios.

The abbreviations used in the present disclosure are explained as follows: the abbreviations of solvents are shown in Table 1.

XRPD: X-ray powder diffraction; DSC: differential scanning calorimetry; TGA: thermogravimetric analysis; DVS: dynamic vapor sorption; 1H-NMR: 1H-nuclear magnetic resonance; HPLC: high performance liquid chromatography; IC: ion chromatography.

TABLE 1

| The name of solvent | The Chinese name of solvent | The name of solvent | The Chinese name of solvent |
|---|---|---|---|
| $H_2O$ | Water | 2-MeTHF | 2-methyltetrahydrofuran |
| MeOH | Methanol | 1,4-Dioxane | 1,4-dioxane |
| EtOH | Ethanol | NMP | N-methylpyrrolidone |
| IPA | Isopropyl alcohol | DMSO | Dimethyl sulfoxide |
| ACN | Acetonitrile | Toluene | Toluene |
| Acetone | Acetone | Heptane | Heptane |

TABLE 1-continued

| The name of solvent | The Chinese name of solvent | The name of solvent | The Chinese name of solvent |
|---|---|---|---|
| MIBK | Methyl isobutyl ketone | Hexane | Hexane |
| EtOAc | Ethyl acetate | MTBE | Methyl tert-butyl ether |
| IPAc | Isopropyl acetate | THF | Tetrahydrofuran |
| DCM | Dichloromethane | $CHCl_3$ | Trichloromethane |
| Isobutyl alcohol | Isobutyl alcohol | Acetic acid | Acetic acid |
| Cyclohexanol | Cyclohexanol | n-Butyl alcohol | n-butyl alcohol |
| n-Amyl alcohol | n-amyl alcohol | sec-Butyl alcohol | sec-butyl alcohol |
| DMF | Dimethyl formamide | 1-Octanol | 1-octanol |
| Diethyl ether | Diethyl ether | tert-Butyl alcohol | tert-butyl alcohol |
| MEK | 2-butanone | Isoamyl alcohol (IAA) | Isoamyl alcohol |

X-ray powder diffraction (XRPD): the XRPD patterns were acquired by a PANalytical Empyrean X-ray powder diffraction analyzer, and the XRPD parameters were shown in Table 2 below.

TABLE 2

| Parameter | Set value |
|---|---|
| X-ray | Cu, lox, $K\alpha1$ (Å): 1.540598; $K\alpha2$ (Å); 1.544426 $K\alpha2/K\alpha1$ intensity ratio: 0.50 |
| X-ray tube settings | 45 kV, 40 mA |
| Divergence slit | Automatic |
| Monochromator | None |
| Scanning mode | Continuous |
| Scanning range (°2 Theta) | 3°~40° |
| Scanning step (°2 Theta) | 0.013 |
| scanning time (min) | 3'56" |

Thermogravimetric analysis (TGA) and differential scanning calorimetry (DSC): the TGA and DSC charts were acquired by a TA Q500/5000 thermogravimetric analyzer and a TA Q200/2000 differential scanning calorimeter, respectively, and the experimental parameters were shown in Table 3 below.

TABLE 3

|  | TGA | DSC | mDSC |
|---|---|---|---|
| Sample disk | Platinum disk, open | Aluminum disk, gland | Aluminum disk, gland |
| Temperature range | RT-250° C. | 25° C.-250° C. | 25° C.-150° C. |
| Scanning rate (° C./min) | 10 | 10 | 3 |
| protective gas | Nitrogen | Nitrogen | Nitrogen |

Dynamic vapor sorption (DVS): Dynamic vapor sorption (DVS) curves were acquired by DVS Intrinsic of SMS (Surface Measurement Systems). The relative humidity at 25° C. was corrected by deliquescence points of LiCl, $Mg(NO_3)_2$ and KCl. The DVS test parameters were shown in Table 4 below.

TABLE 4

| Parameter | Set value |
|---|---|
| Temperature | 25° C. |
| Sample amount | 10-20 mg |
| Protective gas and flow rate | $N_2$, 200 mL/min |
| dmfdt | 0.002%/min |
| Minimum equilibration time | 10 min |
| Maximum equilibration time | 180 min |
| RH range | 47% RH-95% RH-0% RH-95% RH |
| RH gradient | 10% (0% RH-90% RH, 90% RH-0% RH) 5% (90% RH-95% RH, 95% RH-90% RH) 3% (47% RH-50% RH) |

Liquid-state 1H-nuclear magnetic resonance (1H NMR): the liquid-state 1H-nuclear magnetic resonance spectrums were acquired by a Bruker 400M nuclear magnetic resonance spectrometer using DMSO-d6 as a solvent.

Karl Fisher (KF) moisture determination: the moisture test was carried out on a Vantone 870 Karl Fischer moisture titrator, and the used titrant was commercially available Hydranal®-Composite 5 (34805-1L-R, Batch #SZBD-3330V) from Sigma-aldrich. The moisture titrator was corrected with pure water. Methanol (HPLC grade) was used as a solvent.

High performance liquid chromatography (HPLC): the high performance liquid chromatogram was acquired by Agilent 1260 HPLC. The specific instruments and experimental parameters were shown in Table 5 below.

TABLE 5

| Item | Purity test parameter | Stoichiometric ratio test parameter |
|---|---|---|
| Chromatographic column | Waters Xbridge C18 4.6 * 150 mm | Waters Xbridge C18 150 × 4.6 mm |
| Detection wavelength | 220 nm | 230 nm |
| Sample injection volume | 10 mL | 10 mL |
| Flow rate | 1.0 mL/min | 1.0 mL/min |
| Column temperature | 30° C. | 40° C. |
| Sample chamber temperature | RT | RT |
| Mobile phase | A: 0.1% TFA in $H_2O$, B: 0.1% TFA in acetonitrile | A: 0.1% TFA in $H_2O$, B: 0.1% TFA in acetonitrile |
| Time | 32 mins | 10 mins |

Ion chromatography (IC): The ion chromatogram was acquired by ICS 1100. The specific instruments and experimental parameters were shown in Table 6 below.

TABLE 6

| Item | Test parameters |
|---|---|
| Chromatographic column | IonPac AS18 Analytical Column (4 × 250 mm) |
| Mobile phase | 25 mM NaOH |
| Sample injection volume | 25 mL |
| Flow rate | 1.0 mL/min |
| Sample chamber temperature | RT |
| Column temperature | 35° C. |
| Current | 80 mA |
| Time | 28 mins |

The method for preparing the compound of formula (I) in the present disclosure refers to Example 1 in CN103351391B.

Example 1: Method for Preparing Amorphous Phosphate of the Compound of Formula (I)

20 mg of the compound of formula (I) was dissolved in 0.5 mL of methyl tert-butyl ether and then added with phosphoric acid of the same molar amount as the compound of formula (I), the mixture was stirred and reacted for 12 h at the room temperature (25±2° C.), and the solid was collected.

Figure 2:
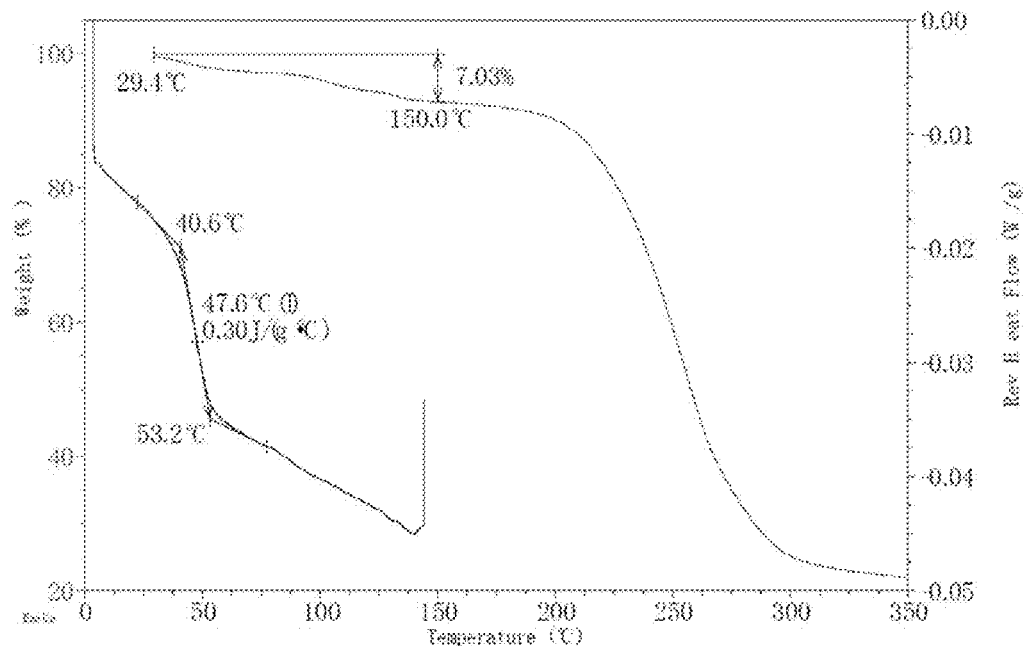
FIG. 2 shows a TGA chart and a DSC chart of amorphous phosphate in Example 1.
Figure 3:
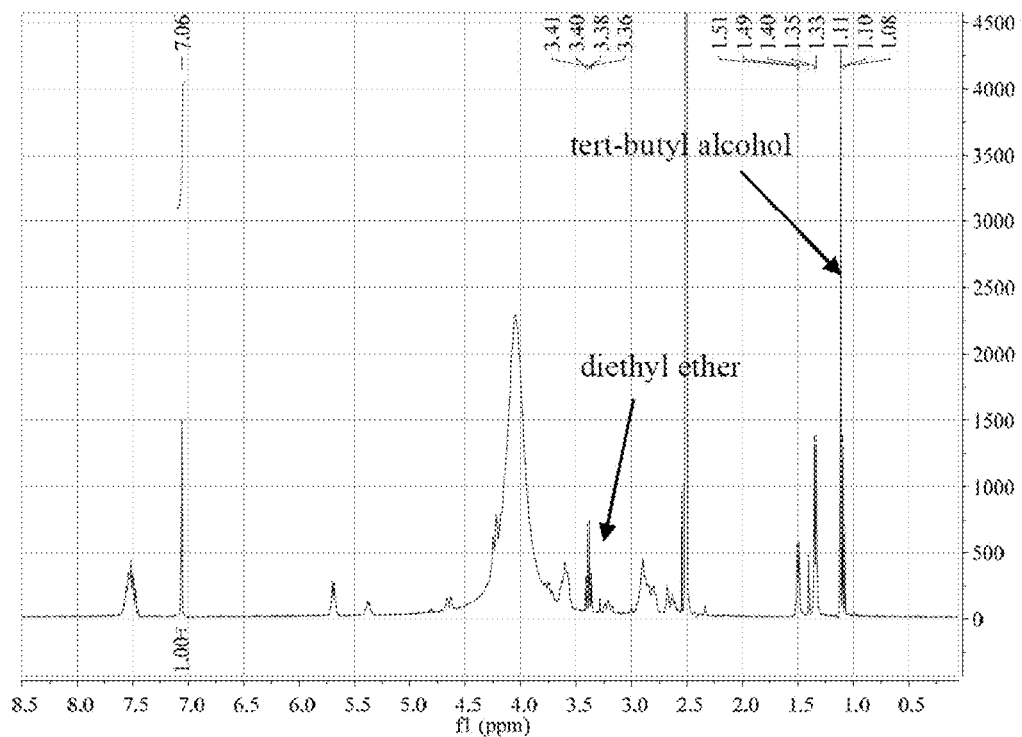
FIG. 3 shows a 1H NMR spectrum of amorphous phosphate in Example 1.

After detection, the obtained solid was an amorphous form of phosphate, its XRPD pattern was shown in FIG. 1, its TGA chart and the DSC chart were shown in FIG. 2, and its 1H NMR spectrum was shown in FIG. 3. The XRPD results indicated that the solid was amorphous. The TGA results in FIG. 2 indicated that the sample had a weight loss of 7.0% when heated to 150° C., and the mDSC results indicated that the glass transition temperature of the sample was 47.6° C. (intermediate point temperature). The 1H NMR (DMSO-d6) spectrum in FIG. 3 and the KF result (4.3%) in the following Table 7 indicated that the solid contained residual solvents, i.e., diethyl ether, tert-butyl alcohol and water.

TABLE 7

| Sample No. | Mass/mg | Moisture content/% |
|---|---|---|
| Example 1 | 49.39 | 4.3% |

The rough solubility of the amorphous phosphate prepared in Example 1 was measured. During the test, about 2 mg of the amorphous phosphate prepared in Example 1 was weighed and put into a 3 mL glass bottle, the solvents listed in the following Table 8 were added separately at an amount of 20 microliters/each time, and it was observed whether the sample was completely dissolved. If the sample was still not dissolved completely after 2.0 mL of the solvents was added, the test ended. The rough solubility results were shown in FIG. 8 below.

TABLE 8

| Solvent | Solubility (mg/mL) | Solvent | Solubility (mg/mL) |
|---|---|---|---|
| MeOH | 67.5 < S < 135.0 | 2-MeTHF | 38.3 < S < 57.5 |
| EtOH | 57.5 < S < 115.0 | 1,4-Dioxane | 2.7 < S < 2.9 |
| IPA | 38.3 < S < 57.5 | NMP | 20.0 < S < 40.0 |
| ACN | 57.5 < S < 115.0 | DMSO | 46.0 < S < 115.0 |
| Acetone | 47.5 < S < 95.0 | CHCl₃ | S < 1.3 |
| MEK | 72.5 < S < 145.0 | DCM | S < 1.1 |
| EtOAc | S < 1.1 | Toluene | S < 1.0 |
| IPAc | S < 1.1 | Hexane | S < 1.2 |
| MTBE | S < 0.9 | Heptane | S < 1.3 |
| THF | 46.0 < S < 115.0 | DMF | S < 42.0 |
| H₂O | 21.0 < S < 42.0 | Acetic acid | S < 54.0 |
| MIBK | S < 1.0 | n-butyl alcohol | 60.0 < S < 120.0 |
| isobutyl alcohol | 3.8 < S < 4.7 | sec-butyl alcohol | S < 1.0 |
| cyclohexanol | S < 1.0 | 1- Octanol | S < 0.9 |
| n-amyl alcohol | 6.8 < S < 8.5 | isoamyl alcohol | 10.0 < S < 13.3 |

Comparative Examples 1 to 3

20 mg of the compound of formula (I) was dissolved in 0.5 mL of methanol and then added with phosphoric acid of the same molar amount as the compound of formula (I); the mixture was stirred and reacted for 12 h at the room temperature (25±2° C.), and no solid was obtained; and, the solvent was continuously volatilized at the room temperature, and no solid was yet obtained.

20 mg of the compound of formula (I) was dissolved in 0.5 mL of acetone and then added with phosphoric acid having the same molar amount as the compound of formula (I); the mixture was stirred and reacted for 12 h at the room temperature (25±2° C.), and no solid was obtained; and, the solvent was continuously volatilized at the room temperature, and no solid was yet obtained.

20 mg of the compound of formula (I) was dissolved in 0.5 mL of mixed solvent of isopropyl alcohol and water at a volume ratio of 19:1 and then added with phosphoric acid of the same molar amount as the compound of formula (I): the mixture was stirred and reacted for 12 h at the room temperature (25±2° C.), and no solid was obtained; and, the solvent was continuously volatilized at the room temperature, and no solid was yet obtained.

Example 2: Method for Preparing a Phosphate Crystal Form A of the Compound of Formula (I)

The amorphous phosphate of the compound of formula (I) prepared in Example 1 was dissolved in a mixed solvent of isoamyl alcohol and water at a volume ratio of 19:1, the solution was slowly volatilized, and the solid was collected.

Figure 4:
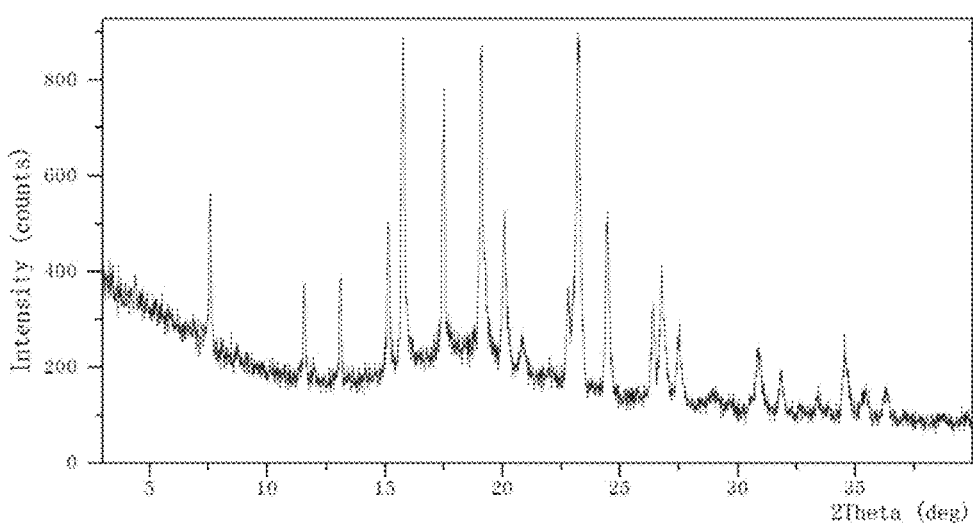
FIG. 4 shows an XRPD pattern of the phosphate crystal form A in Example 2.
Figure 5:
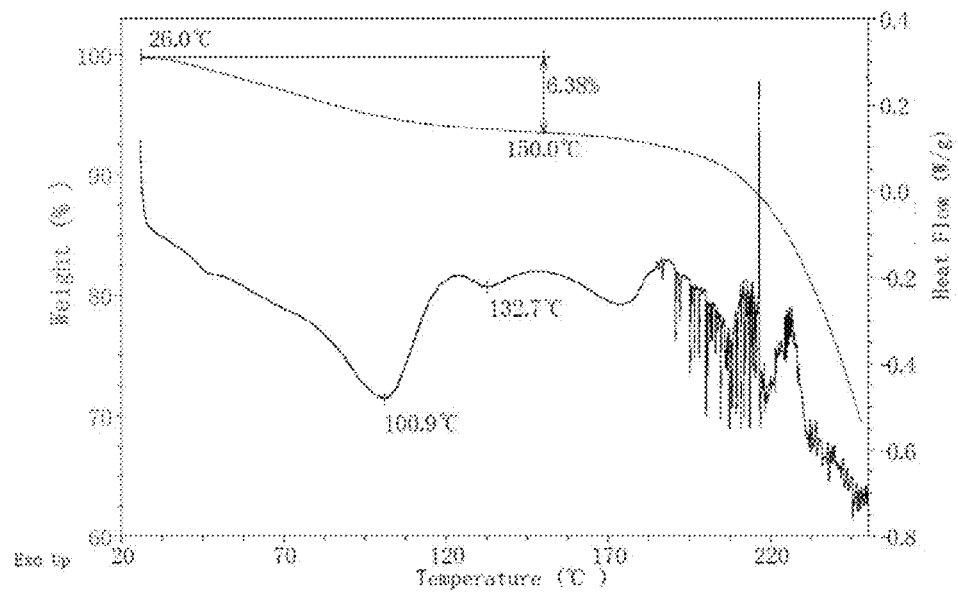
FIG. 5 shows a TGA chart and a DSC chart of the phosphate crystal form A in Example 2.
Figure 6:
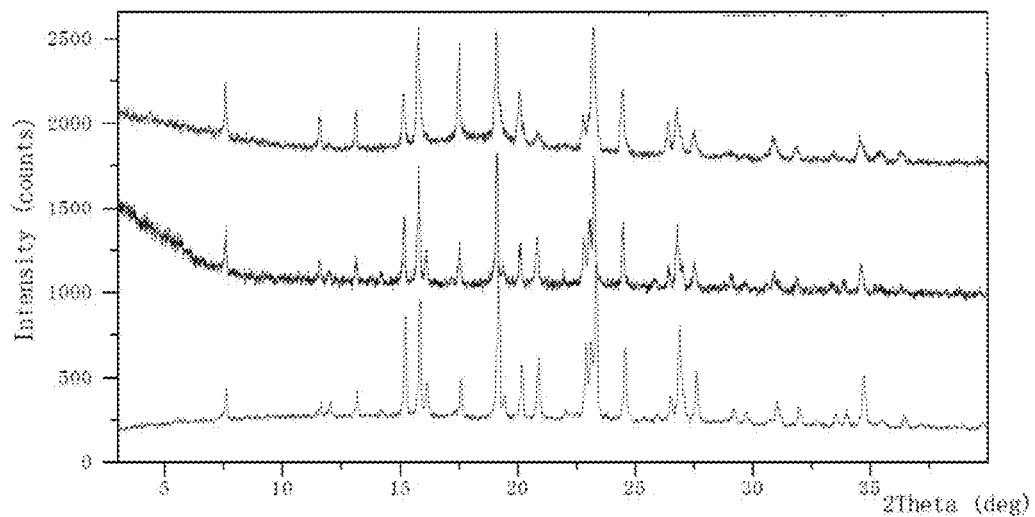
FIG. 6 shows an XRPD pattern when the phosphate crystal form A in Example 2 is transformed into the phosphate crystal form B after being heated at 50° C. for 48 h, wherein the uppermost pattern shows the crystal form A, the middle pattern shows the crystal A being heated to 50° C. and the lowermost pattern shows the crystal form B.

After detection, the obtained solid was the crystal form A of phosphate, its XRPD data was shown in Table 9 below, its XRPD pattern was shown in FIG. 4, and its TGA chart and DSC chart were shown in FIG. 5. The XRPD pattern indicated a high crystallinity, the TGA result indicated that the sample had a weight loss of 6.4% when heated to 150° C., and the DSC result indicated that the sample had two endothermic peaks of 100.9° C. and 132.7° C. (peak temperatures) before decomposition. The XRPD characterization in FIG. 6 indicated that the phosphate crystal form A was transformed into a phosphate crystal form B when heated for 48 h at 50° C.

TABLE 9

| Pos. [° 2Th.] | Height [cts] | FWHM Left [° 2Th.] | d-spacing [Å] | Rel. Int. [%] |
|---|---|---|---|---|
| 7.577782 | 290.493400 | 0.076752 | 11.66665 | 40.53 |
| 11.561770 | 190.838000 | 0.076752 | 7.65393 | 26.63 |
| 13.129840 | 216.880300 | 0.051168 | 6.74315 | 30.26 |
| 15.156900 | 331.927800 | 0.102336 | 5.84559 | 46.31 |
| 15.798400 | 693.338100 | 0.115128 | 5.60964 | 96.73 |
| 17.526440 | 624.520400 | 0.051168 | 5.06025 | 87.13 |
| 19.102670 | 697.087000 | 0.076752 | 4.64612 | 97.26 |
| 20.100730 | 380.054600 | 0.115128 | 4.41763 | 53.02 |
| 20.889780 | 106.578000 | 0.204672 | 4.25251 | 14.87 |
| 22.787580 | 218.167900 | 0.102336 | 3.90247 | 30.44 |
| 23.258060 | 716.750200 | 0.089544 | 3.82458 | 100.00 |
| 24.454170 | 350.611900 | 0.102336 | 3.64016 | 48.92 |
| 26.389640 | 196.984300 | 0.076752 | 3.37741 | 27.48 |
| 26.767600 | 286.495100 | 0.076752 | 3.33057 | 39.97 |
| 27.528020 | 155.227300 | 0.153504 | 3.24027 | 21.66 |
| 28.998000 | 25.064090 | 0.409344 | 3.07928 | 3.50 |
| 30.895330 | 115.140300 | 0.255840 | 2.89436 | 16.06 |
| 31.849150 | 76.281880 | 0.204672 | 2.80983 | 10.64 |
| 33.440670 | 31.247920 | 0.307008 | 2.67965 | 4.36 |
| 34.568630 | 131.049300 | 0.102336 | 2.59476 | 18.28 |
| 35.501440 | 44.878050 | 0.358176 | 2.52869 | 6.26 |
| 36.319760 | 56.399890 | 0.255840 | 2.47357 | 7.87 |

Example 3: Method for Preparing a Phosphate Crystal Form B of the Compound of Formula (I)

15 mg of the amorphous phosphate of the compound of formula (I) prepared in Example 1 was dissolved in 1 mL of ethanol, and the solvent was slowly volatilized at the room temperature (25±2° C.) to obtain solid.

Figure 7:
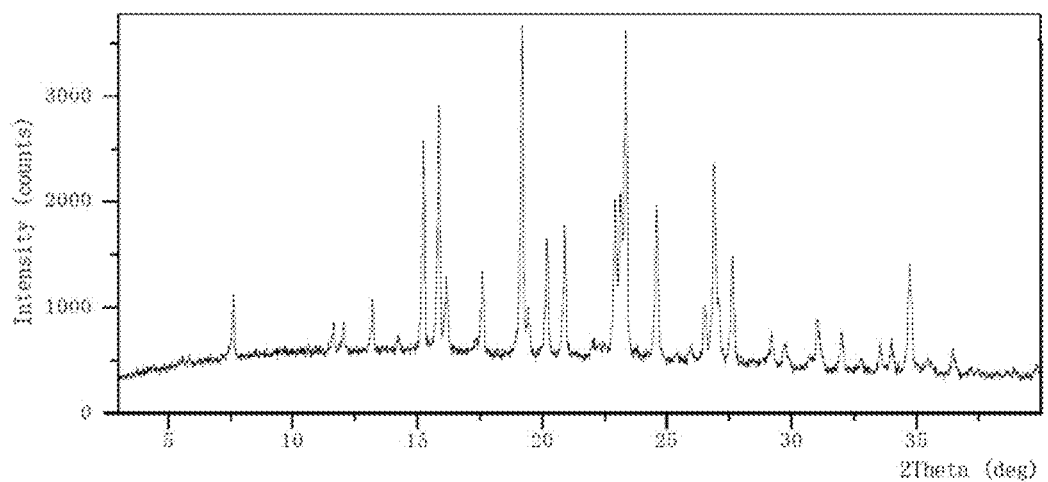
FIG. 7 shows an XRPD pattern of the phosphate crystal form B in Example 3.
Figure 8:
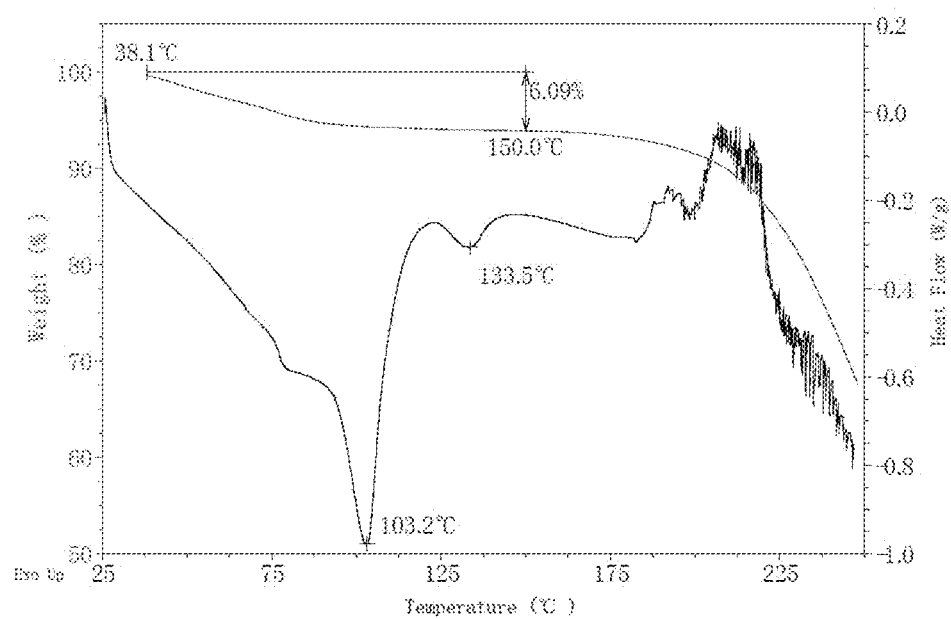
FIG. 8 shows a TGA chart and a DSC chart of the phosphate crystal form B in Example 3.
Figure 9:
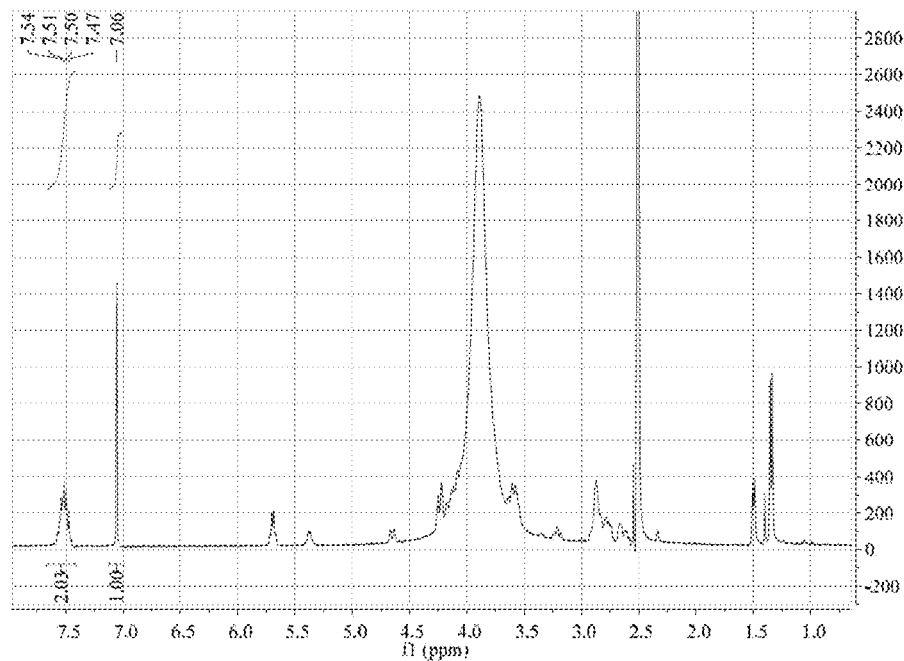
FIG. 9 shows a spectrum showing a 1HNMR characterization result of the phosphate crystal form B in Example 3.

After detection, the obtained solid was the crystal form B of phosphate, its XRPD data was shown in Table 10 below, its XRPD pattern was shown in FIG. 7, its TGA chart and DSC chart were shown in FIG. 8, and the 1H NMR characterization result was shown in FIG. 9. The XRPD indicated that the crystal form had a high crystallinity. The TGA result indicated that the sample had a weight loss of 6.1% when heated to 150° C. The DSC result indicated that the sample had two endothermic peaks of 103.2° C. and 133.5° C. (peak temperature) before decomposition. The 1H NMR (DMSO-d6) spectrum indicated that there was no signal peak of isopropyl alcohol, and it could be determined in combination with the weight loss of the sample of the crystal form B heated in the TGA that the crystal form B was hydrate. The stoichiometric ratio of the reproducible phosphate crystal B preparation was determined by a HPLC/IC method. The results showed that the ratio of free base to phosphoric acid was 1:1.

TABLE 10

| Pos. [°2Th.] | Height [cts] | FWEIM Left [°2Th.] | d-spacing [Å] | Rel. Int. [%] |
| --- | --- | --- | --- | --- |
| 7.628860 | 518.496800 | 0.063960 | 11.58865 | 16.56 |
| 11.639310 | 237.923800 | 0.076752 | 7.60311 | 7.60 |
| 12.054270 | 303.217200 | 0.089544 | 7.34229 | 9.68 |
| 13.191720 | 504.178400 | 0.063960 | 6.71166 | 16.10 |
| 14.198440 | 146.095500 | 0.127920 | 6.23796 | 4.67 |
| 15.237740 | 2024.046000 | 0.076752 | 5.81476 | 64.65 |
| 15.860860 | 2356.759000 | 0.076752 | 5.58769 | 75.27 |
| 16.147810 | 753.388100 | 0.063960 | 5.48904 | 24.06 |
| 17.595680 | 818.773300 | 0.063960 | 5.04050 | 26.15 |
| 19.193610 | 3114.213000 | 0.089544 | 4.62043 | 99.46 |
| 19.446430 | 490.417100 | 0.076752 | 4.56476 | 15.66 |
| 20.177690 | 1100.112000 | 0.089544 | 4.40095 | 35.14 |
| 20.904420 | 1180.684000 | 0.089544 | 4.24957 | 37.71 |
| 22.920140 | 1534.668000 | 0.063960 | 3.88020 | 49.02 |
| 23.125720 | 1585.832000 | 0.089544 | 3.84617 | 50.65 |
| 23.345300 | 3130.967000 | 0.089544 | 3.81049 | 100.00 |
| 24.578980 | 1467.029000 | 0.102336 | 3.62195 | 46.86 |
| 25.964660 | 189.230800 | 0.153504 | 3.43172 | 6.04 |
| 26.502740 | 555.451200 | 0.076752 | 3.36325 | 17.74 |
| 26.889870 | 1919.549000 | 0.076752 | 3.31571 | 61.31 |
| 27.625140 | 1035.070000 | 0.063960 | 3.22910 | 33.06 |
| 29.199130 | 315.324400 | 0.102336 | 3.05852 | 10.07 |
| 29.705760 | 213.022900 | 0.127920 | 3.00750 | 6.80 |
| 31.033300 | 492.411200 | 0.063960 | 2.88181 | 15.73 |
| 31.997340 | 368.055100 | 0.063960 | 2.79715 | 11.76 |
| 32.778950 | 117.339100 | 0.102336 | 2.73222 | 3.75 |
| 33.534000 | 237.431800 | 0.102336 | 2.67241 | 7.58 |
| 34.002840 | 269.202400 | 0.127920 | 2.63662 | 8.60 |
| 34.727690 | 1025.108000 | 0.076752 | 2.58324 | 32.74 |
| 35.499200 | 106.897500 | 0.255840 | 2.52884 | 3.41 |
| 36.463850 | 245.617600 | 0.051168 | 2.46413 | 7.84 |

Figure 10:
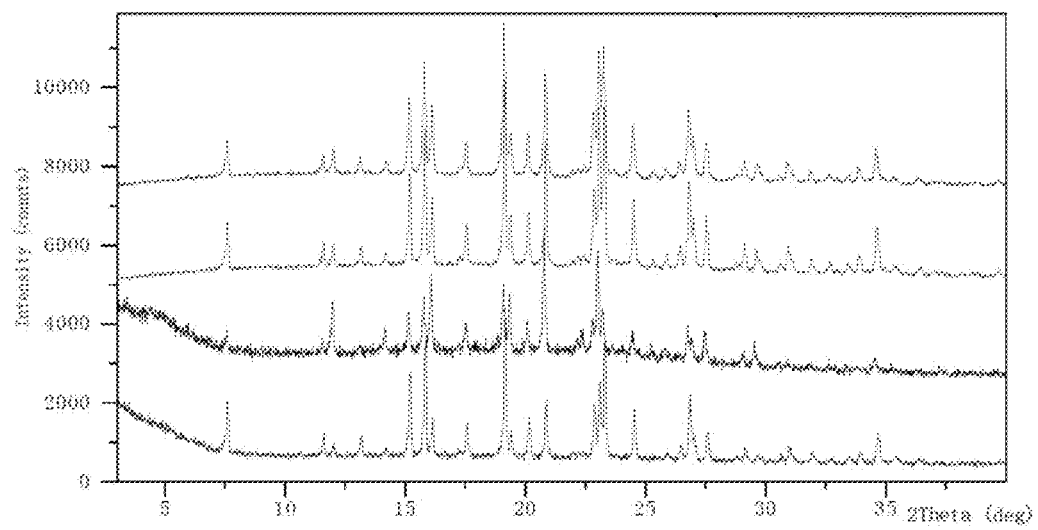
FIG. 10 shows an XRPD overlay pattern of the phosphate crystal form B in Example 3 showing the stability of the phosphate crystal form B, wherein the uppermost pattern shows 40° C./75% RH, 1 week; the second pattern shows 25° C./60% RH, 1 week: the third pattern shows 80° C., 24 h; and the lowermost pattern shows Initial.
Figure 11:
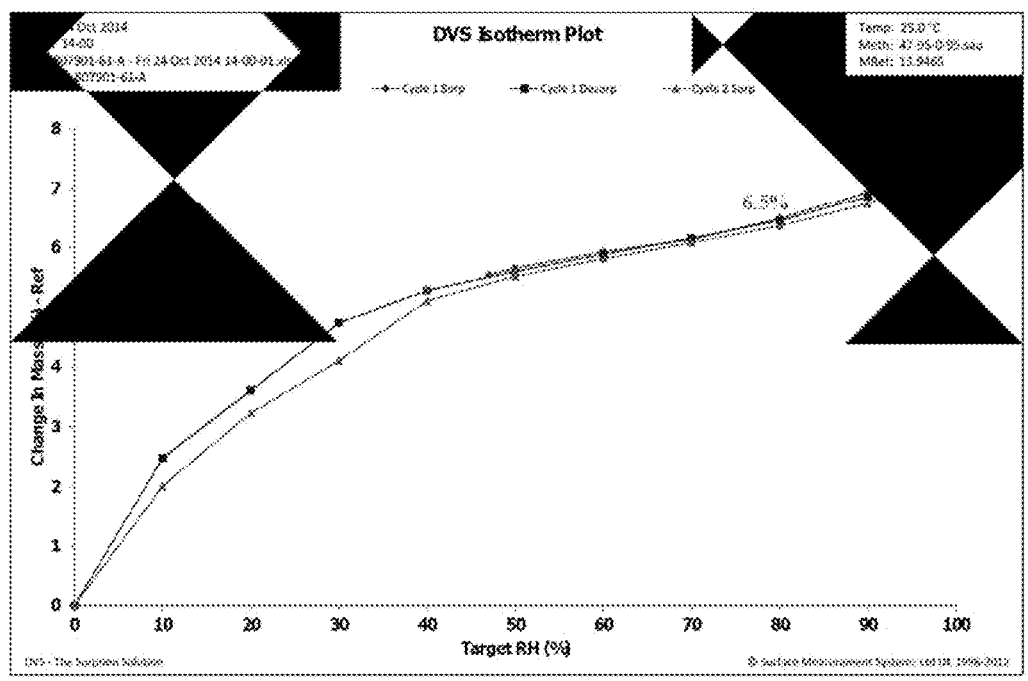
FIG. 11 shows a DVS chart of the phosphate crystal form B in Example 3.
Figure 12:
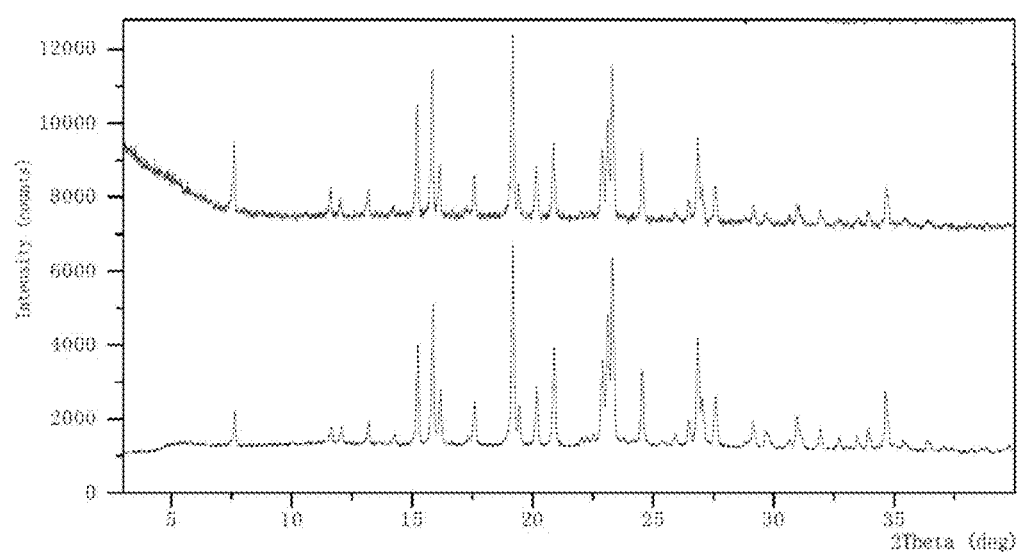
FIG. 12 shows an XRPD pattern before and after the DVS test, wherein the upper shows the XRPD pattern before the DVS test and the lower shows the XRPD pattern after the DVS test.

Research on Physical Properties:

The crystal form B of phosphate prepared in this example was put into a 1.5 mL small bottle and the small bottles was placed under different conditions: 40° C./75% RH or 25° C./60% RH for one week in an open state, or 80° C. for 24 h. The obtained samples were subjected to XRPD test and HPLC test, and the sealed samples placed at 5° C. were used as reference samples (Initial) for HPLC purity test. The samples placed at 80° C. for 24 h changed from white solid into yellow solid in appearance. The results in FIG. 10 and the following Table 11 showed that the XRPD of the samples remained unchanged in the one-week stability test, that is, no crystal form was changed; and, the purity did not change significantly, that is, the phosphate crystal form B had good physical and chemical stability under the test conditions. The DVS results in FIG. 11 indicated that the moisture absorption/desorption of the samples changed smoothly in a range from 25° C./40% RH to 25° C./80% RH. The weight gain at 25° C./80% RH is 6.5% compared to 0% RH. The XRPD results in FIG. 12 showed that XRPD pattern for the phosphate crystal form B had kept the same before and after the DVS test and the crystal form remained unchanged.

TABLE 11

| Sample | Placement condition | Crystal form | Purity (area %) |
| --- | --- | --- | --- |
| Phosphate crystal form B | Initial | Phosphate crystal form B | 99.78 |
| | 40° C./75% RH, one week | Phosphate crystal form B | 99.64 |
| | 25° C./60% RH, one week | Phosphate crystal form B | 99.65 |
| | 80° C., 24 h | Phosphate crystal form B | 99.48 |

Research on the Relationship Between the Plasma Concentration of the Crystal Form B of the Phosphate and the Activity of Serum DPPIV:

Test samples and positive drug: the crystal form B of phosphate (named DPPIV-P1) prepared in Example 3. A solution with a certain concentration was prepared from the crystal form B of the phosphate, and the administration volume was 10 mL/kg. Sitagliptin phosphate was used as a positive control drug to prepare a solution, and the administration volume was 10 mL/kg.

Experimental animals: CD-1 (ICR) mice aged for 4 weeks and weighed for about 18-22 g.

Grouping and administration scheme: the mice were fed adaptively, randomly grouped according to the weight on the day before experiment, and fasted overnight. The experiment was carried out in 6 groups: (1) a negative control group; (2) sitagliptin phosphate 3 mg/kg group; (3) DPPIV-P1 0.1 mg/kg group; (4) DPPIV-P1 0.3 mg/kg group; (5) DPPIV-P1 1 mg/kg group; (6) DPPIV P1 3 mg/kg group; and another group was provided separately for detecting the initial basic value of DPPIV. After the experimental grouping, the group provided separately for detecting the initial basic value of DPPIV was carried out blood sampling, and other animals were intragastrically administrated with the drug at an administration volume of 10 mL/kg, the blood was sampled after the administration, and all other animals were stimulated with glucose administration; the blood was sampled at 20 min, 40 min, 60 min and 120 min after the glucose administration, respectively, and the plasma concentration and the DPPIV activity were detected by using plasma. The DPPIV-P1 had an influence on the weight of the animals, and the weight data of each group was shown in Table 12.

TABLE 12

| Group and dose (mg/kg) | | | | | |
| --- | --- | --- | --- | --- | --- |
| Negative control | Sitagliptin phosphate-3 | DPPIV-P1-0.1 | DPPIV-P1-0.3 | DPPIV-P1-1 | DPPIV-P1-3 |
| 23.5 | 22.2 | 24.8 | 22.0 | 26.4 | 24.1 |
| 25.7 | 24.6 | 24.9 | 22.6 | 25.2 | 25.2 |
| 26.3 | 26.5 | 26.2 | 25.0 | 22.4 | 27.2 |

TABLE 12-continued

| Negative control | Sitagliptin phosphate-3 | DPPIV-P1-0.1 | DPPIV-P1-0.3 | DPPIV-P1-1 | DPPIV-P1-3 |
|---|---|---|---|---|---|
| 21.0 | 26.0 | 24.2 | 24.4 | 23.4 | 24.5 |
| 24.2 | 24.0 | 22.0 | 25.3 | 26.9 | 25.0 |
| 25.4 | 26.0 | 24.5 | 24.0 | 25.1 | 24.8 |
| 26.4 | 25.1 | 24.7 | 24.1 | 23.5 | 23.0 |
| 26.5 | 25.0 | 25.1 | 23.9 | 23.6 | 25.4 |
| 23.3 | 24.6 | 26.3 | 25.3 | 24.9 | 21.7 |
| 25.5 | 24.0 | 26.9 | 24.9 | 24.8 | 27.3 |
| 23.2 | 24.4 | 24.6 | 24.6 | 25.1 | 22.3 |
| 23.0 | 24.3 | 23.4 | 26.4 | 26.1 | 22.4 |
| 23.2 | 22.9 | 24.4 | 26.0 | 24.9 | 25.7 |
| 23.1 | 25.1 | 25.0 | 25.5 | 25.8 | 24.0 |
| 22.9 | 24.0 | 23.0 | 24.9 | 23.6 | 23.3 |

Figure 28:
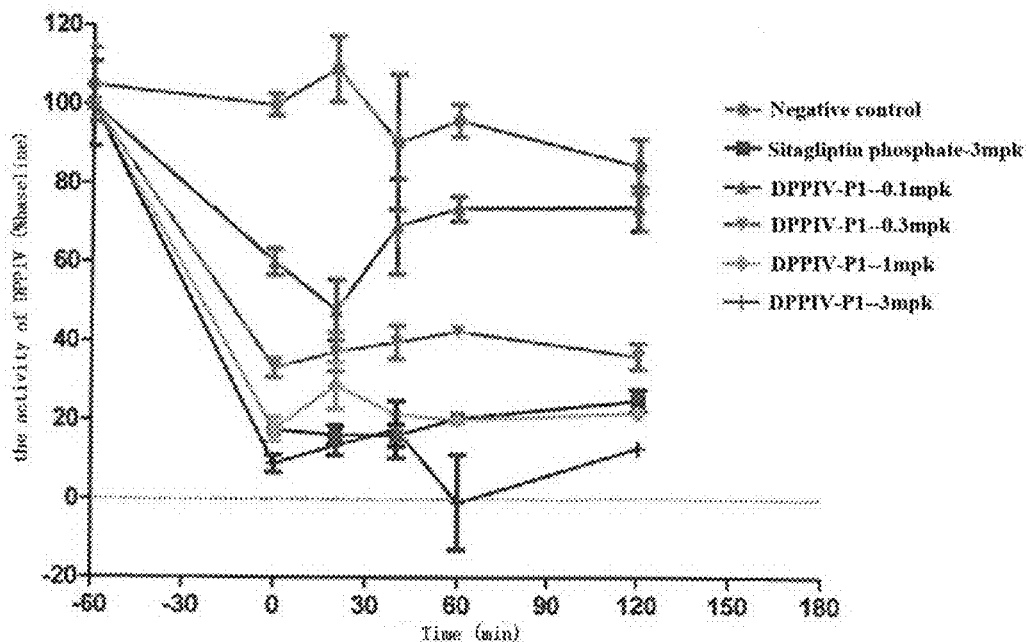
FIG. 28 shows the influence of the phosphate crystal form B on DPPIV in ICR mice (mean value f standard deviation, n=3)

The influence of DPPIV-P on the activity of serum DPPIV of the ICR mice was as follows: FIG. 28 showed the result of DPPIV activity detection, and it could be seen from FIG. 28 that the DPPIV-P1 had a good dose-effect relationship with the activity of serum DPPIV of the ICR mice.

Research on pharmacodynamics-plasma concentration correlation: blood samples were collected at time points of 1 h, 1.33 h, 1.67 h, 2 h and 3 h after administration, and the plasma concentration was measured. The results were shown in Table 13 below. The drug exposure value ($AUC_{eff0-3h}$) of the DPPIV-P1 increased with the increase of dose, which was 16.09 ng·h/mL, 52.65 ng·h/mL, 162.3 ng·h/mL and 542.28 ng·h/mL, respectively. Meanwhile, in the case of the same dose, the drug exposure value ($AUC_{eff0-3h}$) of the DPPIV-P1 3 mg/kg group was higher than the drug exposure value ($AUC_{eff0-3h}$) of the sitagliptin phosphate 3 mg/kg group, wherein the drug exposure values of the two groups were 542.28 ng·h/mL and 369.74 ng·h/mL, respectively.

TABLE 13

| Time | Sitagliptin phosphate | DPPIV-P1 | DPPIV-P1 Oral dose | DPPIV-P1 | DPPIV-P1 |
|---|---|---|---|---|---|
| | 3 mg/kg | 0.1 mg/kg | 0.3 mg/kg | 1 mg/kg | 3 mg/kg |
| 1 hour | 183.54 ± 10.20 | 8.28 ± 0.96 | 26.38 ± 6.47 | 72.83 ± 7.04 | 231.38 ± 16.64 |
| 1.33 hours | 159.31 ± 46.65 | 6.51 ± 1.58 | 25.01 ± 3.42 | 71.91 ± 2.71 | 291.5 ± 47.19 |
| 1.67 hours | 151.76 ± 15.10 | 6.46 ± 0.20 | 17.88 ± 2.43 | 75.2 ± 6.09 | 242.38 ± 17.66 |
| 2 hours | 142.16 ± 19.59 | 5.73 ± 0.65 | 20.52 ± 0.32 | 57.89 ± 2.06 | 201.41 ± 44.69 |
| 3 hours | 97.89 ± 35.52 | 4.85 ± 0.25 | 14.18 ± 1.48 | 52.18 ± 5.54 | 151.24 ± 26.40 |
| Drug exposure **($AUC_{eff0-3\,h}$) | 369.74 ng · h/mL | 16.09 ng · h/mL | 52.65 ng · h/mL | 162.3 ng · h/mL | 542.28 ng · h/mL |

*the unit of the plasma concentration was ng/mL, and **the drug exposure value was $AUC_{eff0-3\,h}$ in unit of ng · h/mL.

Conclusion: during the PK/PD experiment of ICR mice, the blood samples were collected at 1 h, 1.33 hours, 1.67 hours, 2 hours and 3 hours after administration to detect the concentration of the compound and the DPPIV activity so as to preliminarily know the correlation between the pharmacological effect and the plasma concentration. In this model, the DPPIV-P1 inhibited the activity of DPPIV in a dose dependent manner, and the drug exposure value of the DPPIV-P1 increased with the increase of administration dose, so that a good dose dependence relationship was shown. Meanwhile, in the case of the same dose, the drug exposure value ($AUC_{eff0-3h}$) of the DPPIV-P1 was slightly higher than the drug exposure value ($AUC_{eff0-3h}$) of the sitagliptin phosphate, wherein the drug exposure values were 542.28 ng·h/mL and 369.74 ng·h/mL, respectively. This also indicated that the DPPIV-P1 had higher oral bioacailability than the sitagliptin phosphate.

Research on the Hypoglycemic Effect of the Long-Term Administration of the Crystal Form B of Phosphate on DIO Mice Test samples and positive drug: the crystal form B of phosphate (named DPPIV-P1) prepared in Example 3. A solution with a certain concentration was prepared from the crystal form B of the phosphate, and the administration volume was 10 mL/kg. Sitagliptin phosphate was used as a positive control drug to prepare a solution, and the administration volume was 10 mL/kg.

Experimental animals: C57BL16 mice aged for 5 weeks and weighed for about 13-16 g.

Grouping and administration scheme: the mice were fed adaptively and divided into a normal control group and a model group which were fed with high-fat feed (Research diets, D 12492). When the fasting blood glucose of the mice was greater than or equal to 7 mM, it was considered that the mice had become DIO mice. The DIO mice could be selected for the hypoglycemic effect test. The DIO mice were stratified and randomly grouped according to the blood glucose and the weight. The experiment was carried out in 6 groups: (1) a lean mice control group; (2) a model control group; (3) sitagliptin phosphate 30 mg/kg; (4) DPPIV-P1 0.3 mg/kg; (5) DPPIV-P1 3 mg/kg; (6) DPPIV-P1 30 mg/kg; after the beginning of the experiment, the animals were intragastrically administered with the drug every day at an administration volume of 10 ml/kg. The weight and the fasting blood glucose were measured weekly; the food amount, the remaining food amount and the food intake were recorded; the mice were fasted overnight at the end of administration, the blood was sampled, and the free fatty acid (NEFA), total cholesterol (TCHO), triglyceride (TG), insulin and DPPIV activity were measured by using serum.

Figure 29:
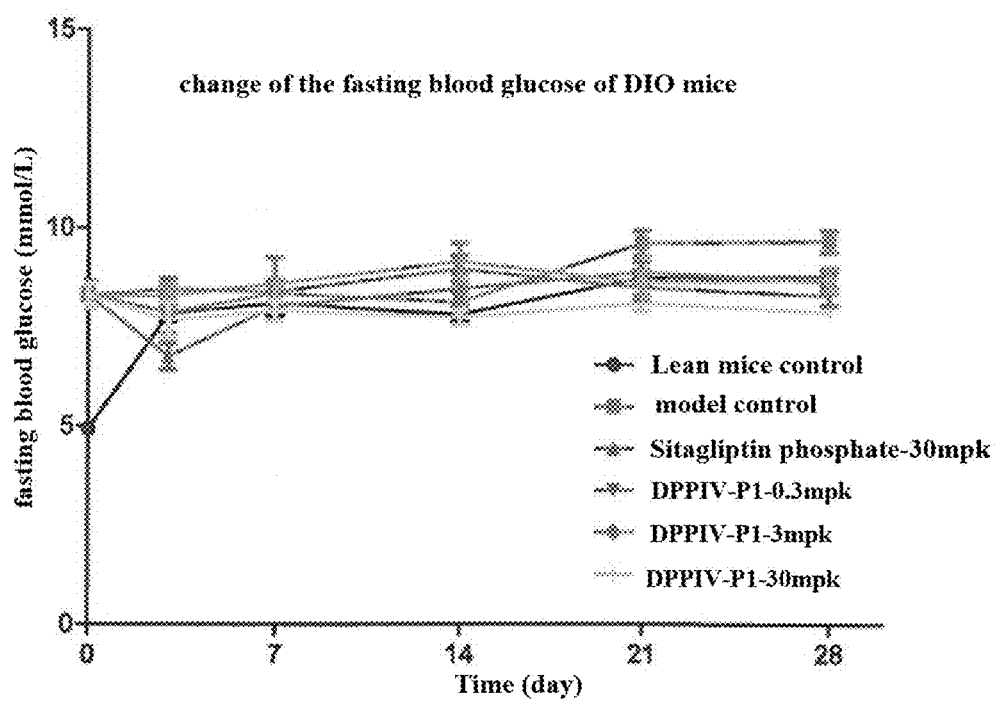
FIG. 29 shows the influence of the long-term administration of DPPIV-P1 on the fasting blood glucose of DIO mice (mean value±standard deviation, n=11)
Figure 30:
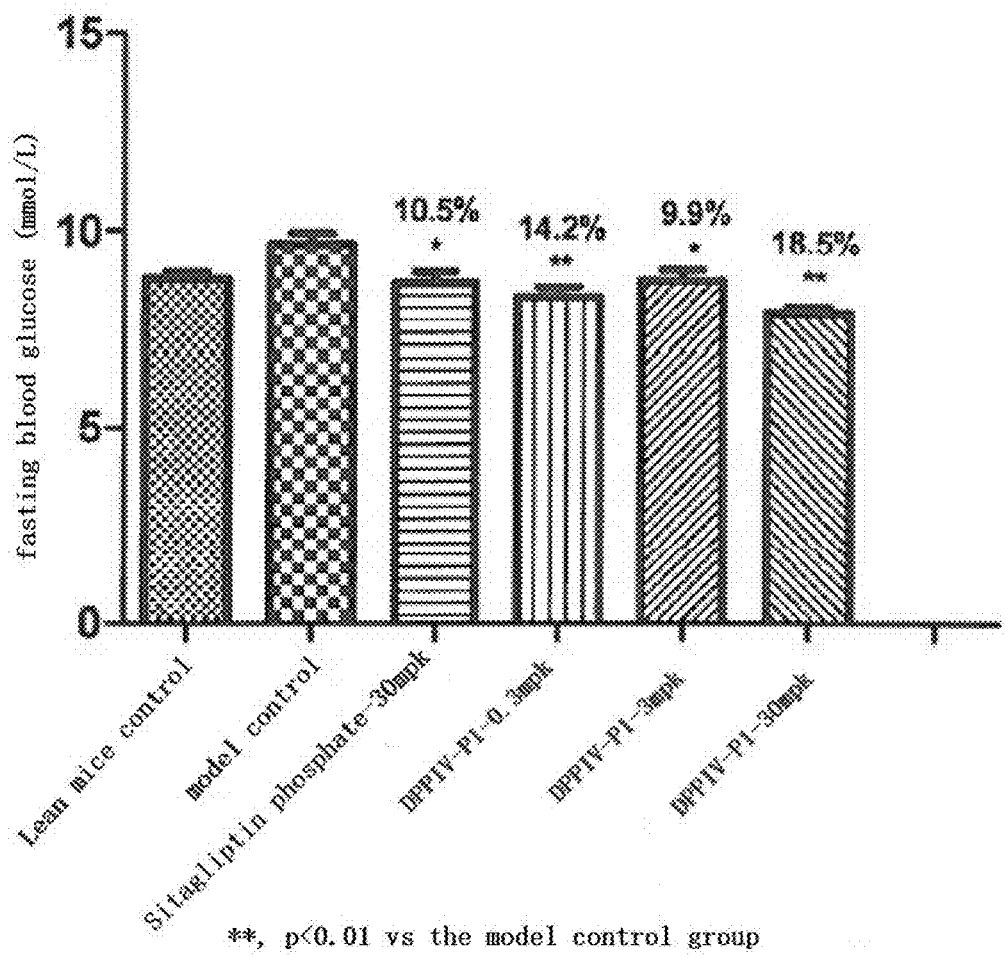
FIG. 30 shows the result of the fasting blood glucose data and the inhibition rate of each group when the DPPIV-P1 is administrated for 28 days, wherein the inhibition rate is the result compared with the model control group (mean value±standard deviation, n=11)

The influence of DPPIV-P1 on the blood glucose level of the DIO mice was as follows: Table 14 and FIG. 29 showed the results of glucose monitoring during the experiment, and Table 15 and FIG. 30 showed the fasting blood glucose data after the drug was administrated for 28 days. The results showed that, at the end of the experiment, the DPPIV-P1 inhibited the rise of the blood glucose in a dose dependent manner. The inhibition rate was 14.2%, 9.9% and 18.5%, respectively, which were significantly or extremely significantly different from that of the model control group (p<0.05 or 0.01).

TABLE 14

| Group and dose (mg/kg) | Fasting blood glucose (mmol/L) | | | | | |
|---|---|---|---|---|---|---|
| | D 1 | D 3 | D 7 | D 14 | D 21 | D 28 |
| Lean mice control | 4.9 ± 0.4 | 7.8 ± 0.6 | 8.1 ± 1.0 | 7.8 ± 0.6 | 8.7 ± 0.7 | 8.8 ± 0.5 |
| Model control | 8.3 ± 1.1 | 7.9 ± 1.7 | 8.3 ± 0.7 | 8.1 ± 0.9 | 9.6 ± 1.1 | 9.7 ± 0.9 |
| Sitagliptin phosphate-30 | 8.3 ± 1.1 | 6.8 ± 1.1 | 8.0 ± 1.2 | 8.5 ± 1.3 | 8.9 ± 0.9 | 8.6 ± 0.9* |
| DPPIV-P1-0.3 | 8.3 ± 1.1 | 8.4 ± 0.9 | 8.4 ± 1.0 | 8.9 ± 1.1 | 8.5 ± 1.0* | 8.3 ± 0.8** |
| DPPIV-P1-3 | 8.3 ± 1.1 | 8.3 ± 0.9 | 8.6 ± 2.2 | 9.1 ± 1.6 | 8.6 ± 1.0* | 8.7 ± 0.9* |
| DPPIV-P1-30 | 8.3 ± 1.0 | 7.8 ± 1.5 | 7.9 ± 0.8 | 7.7 ± 0.7 | 8.1 ± 0.6** | 7.9 ± 0.6** |

In this table: compared with the model control group,
*indicated that p < 0.05;
**indicated that p < 0.01

TABLE 15

| Group and dose (mg/kg) | | | | | |
|---|---|---|---|---|---|
| Lean mice control | Model control | Sitagliptin phosphate-30 | DPPIV-P1-0.3 | DPPIV-P1-3 | DPPIV-PI-30 |
| 8.4 | 10.7 | 7.9 | 8.3 | 7.8 | 8.2 |
| 8.5 | 11.3 | 8 | 8.6 | 8 | 7.8 |
| 8.9 | 8.8 | 10.8 | 7.3 | 8.3 | 7.4 |
| 9.1 | 9 | 7.9 | 7.9 | 10 | 7.4 |
| 8.7 | 10.1 | 8.9 | 10.3 | 9.2 | 8.5 |
| 9.3 | 10.3 | 8.3 | 8 | 7.8 | 7.3 |
| 9.9 | 10.4 | 8.4 | 7.3 | 9.8 | 7.4 |
| 8.4 | 9.4 | 7.8 | 8.8 | 8.9 | 7.6 |
| 8.2 | 8.9 | 9.1 | 8 | 9 | 8.9 |
| 8.9 | 8.7 | 8.2 | 8 | 7.3 | 8.2 |
| 8.2 | 8.7 | 9.8 | 8.7 | 9.7 | 7.5 |

Figure 31:
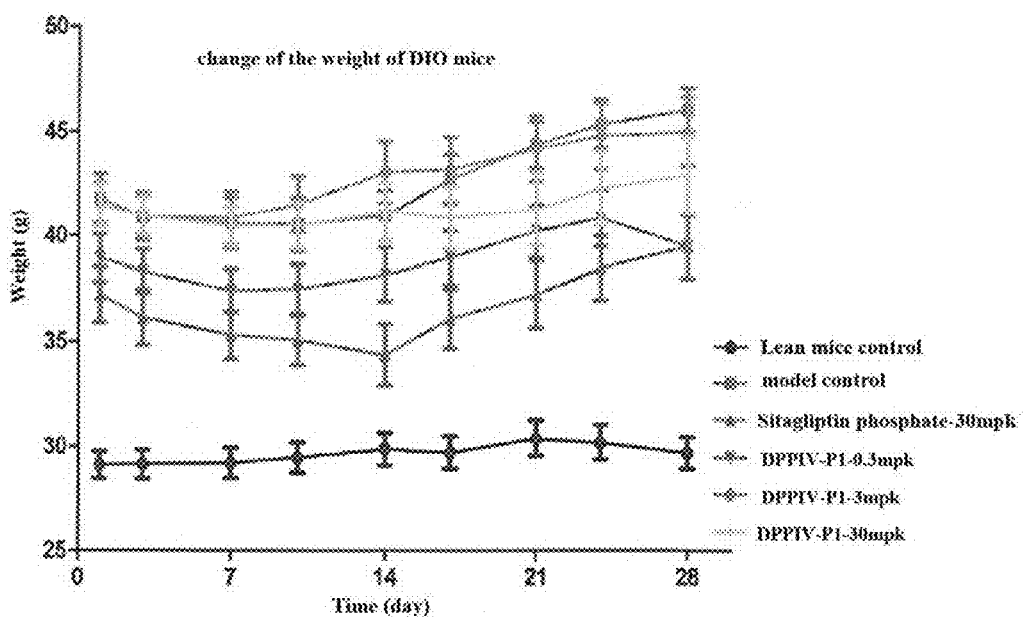
FIG. 31 shows the influence of the long-term administration of DPPIV-P1 on the weight of DIO mice (mean value±standard deviation, n=1)
Figure 32:
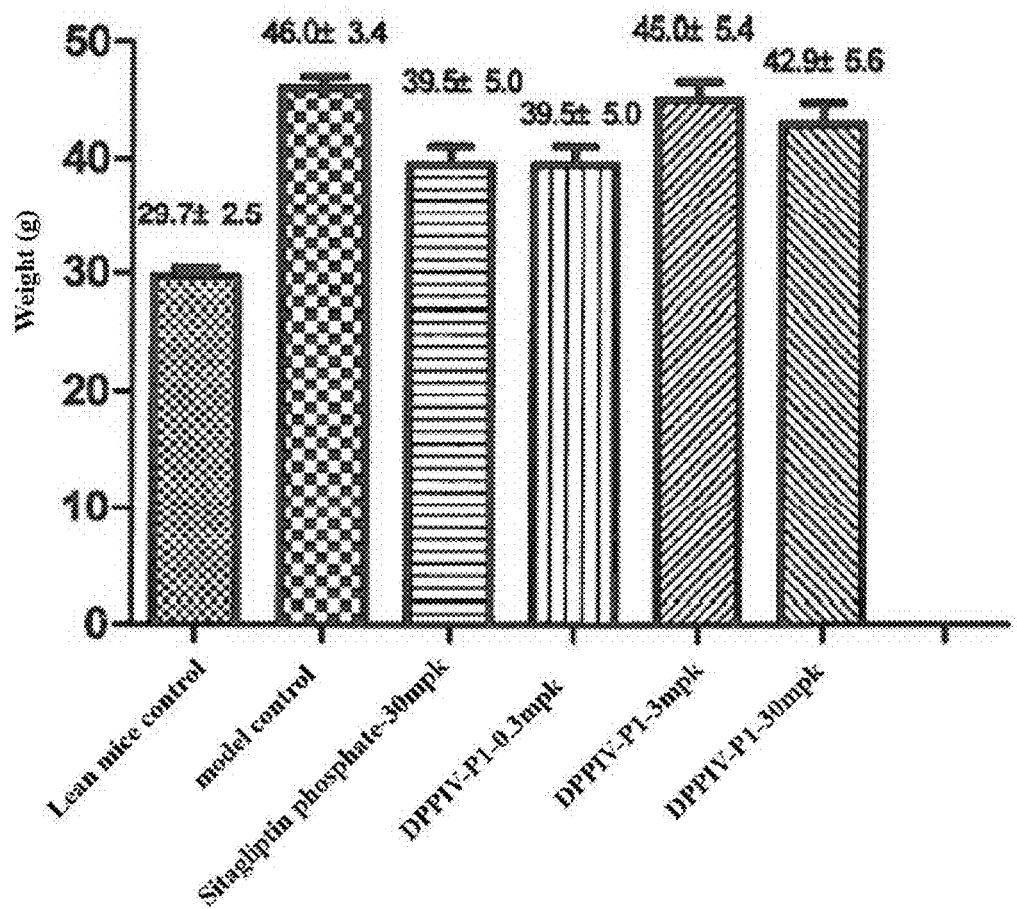
FIG. 32 shows the weight data of each group when the DPPIV-P1 is administrated for 28 days (mean value±standard deviation, n=11)
Figure 33:
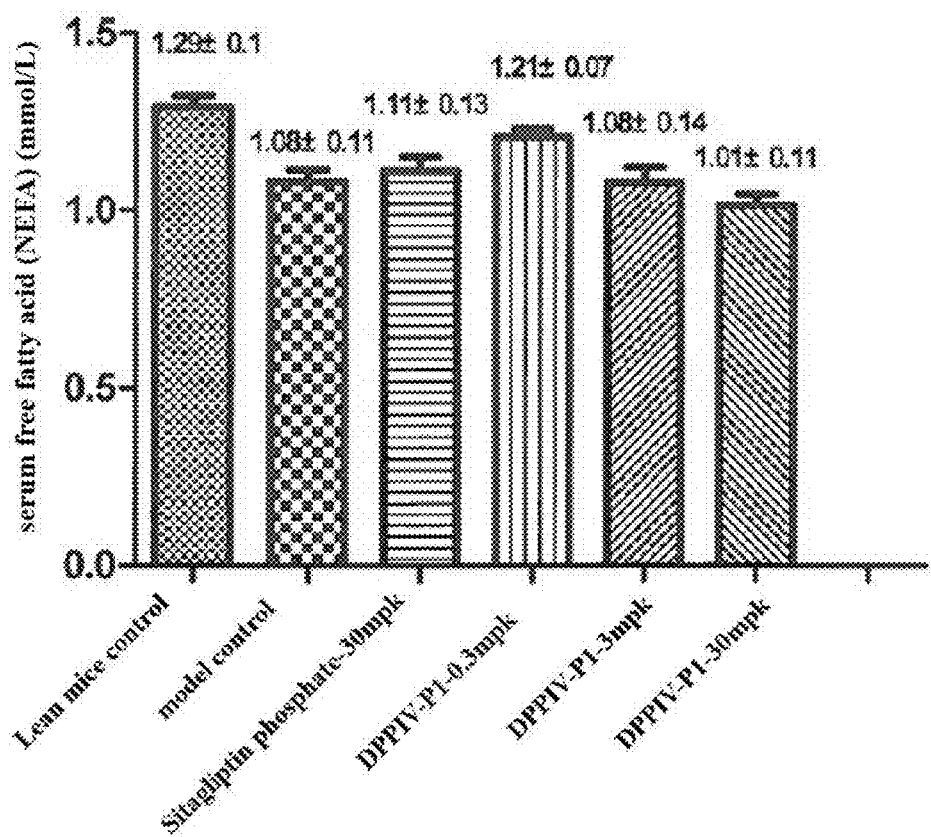
FIG. 33 shows free fatty acid (NEFA) data of serum of each group (mean value=standard deviation, n=11)
Figure 34:
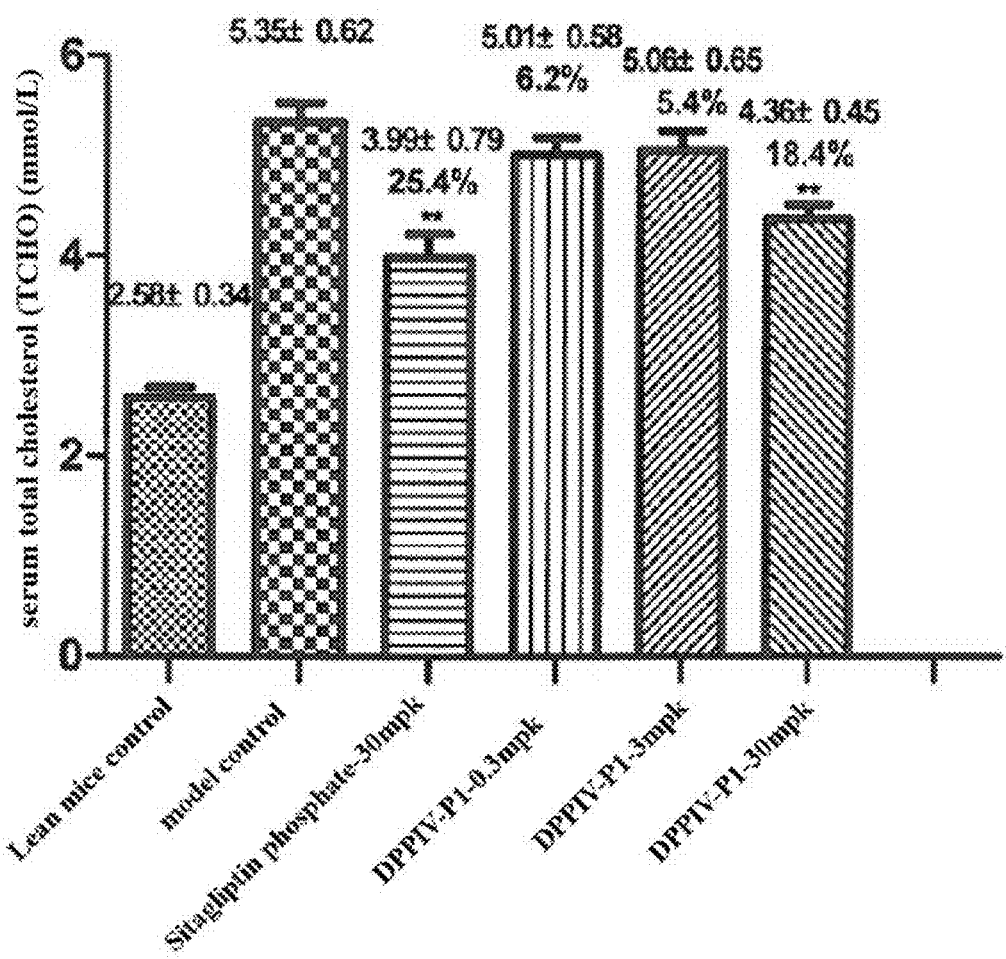
FIG. 34 shows total cholesterol (TCHO) data of serum of each group (mean value±standard deviation, n=11)
Figure 35:
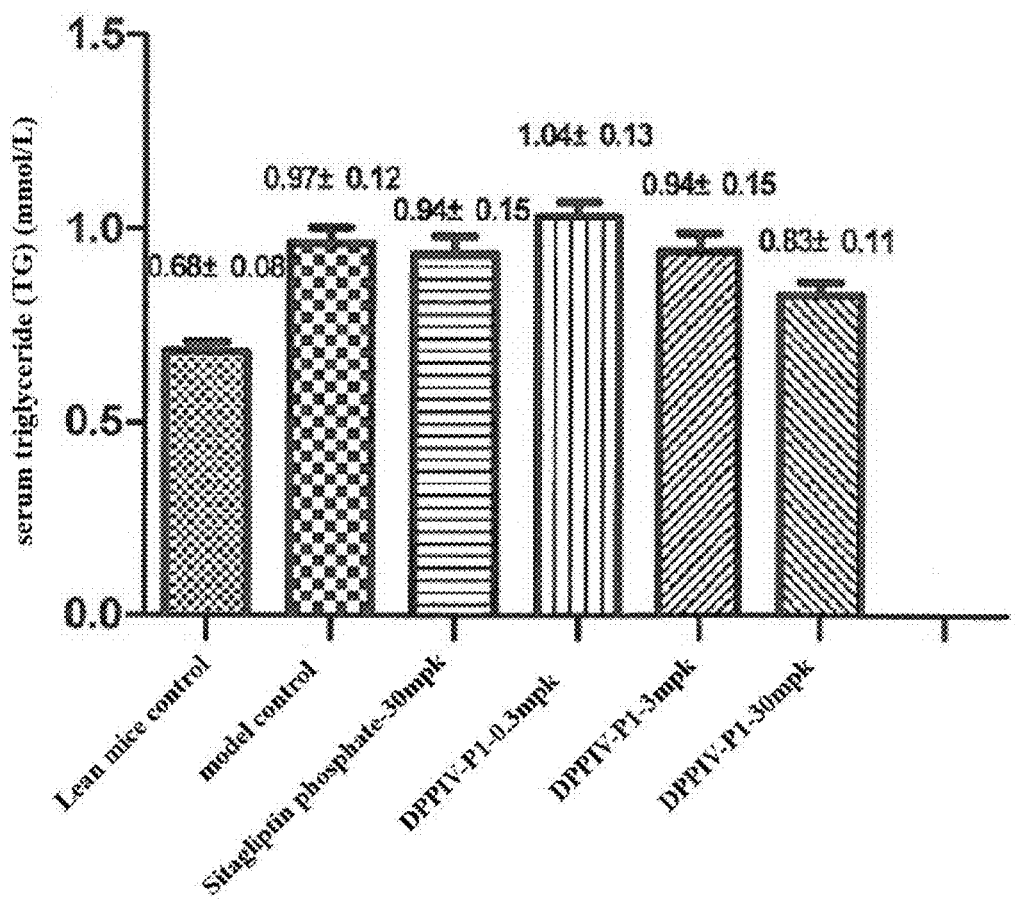
FIG. 35 shows triglyceride (TG) data of serum of each group (mean value±standard deviation, n=1)
Figure 36:
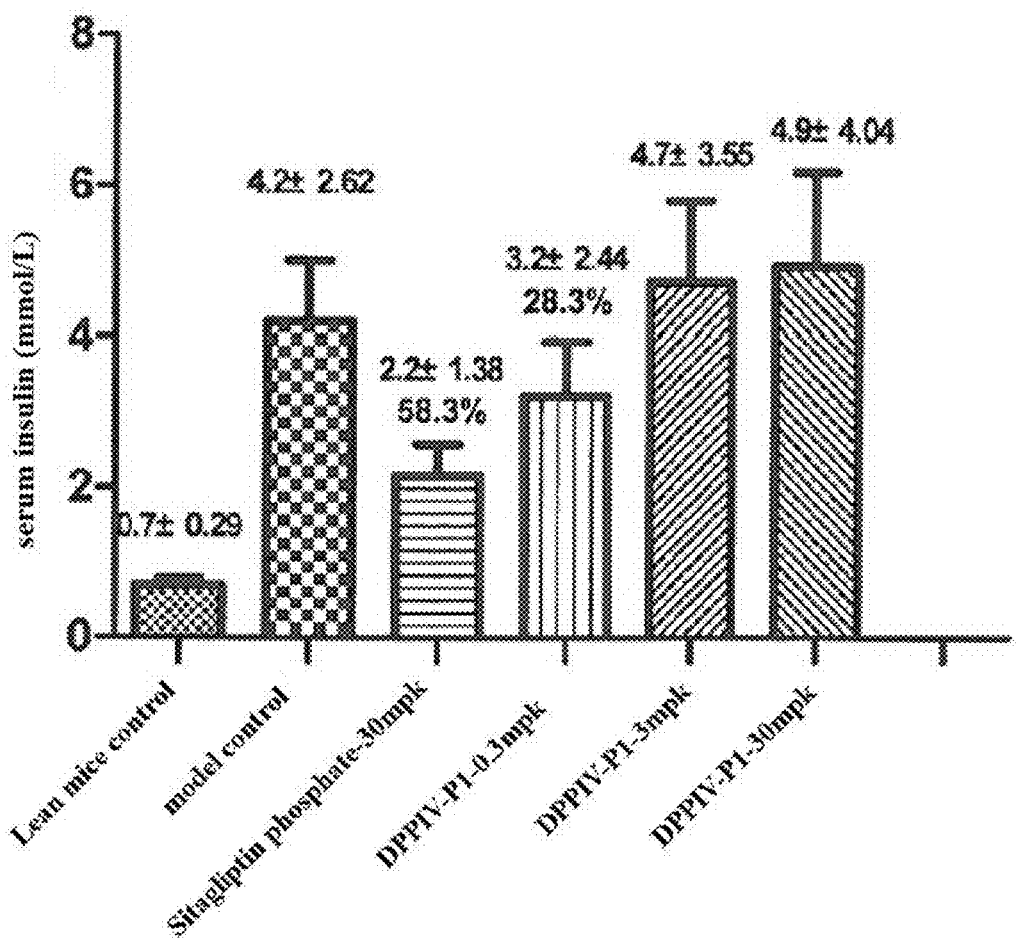
FIG. 36 shows insulin data of serum of each group (mean value±standard deviation, n=11)
Figure 37:
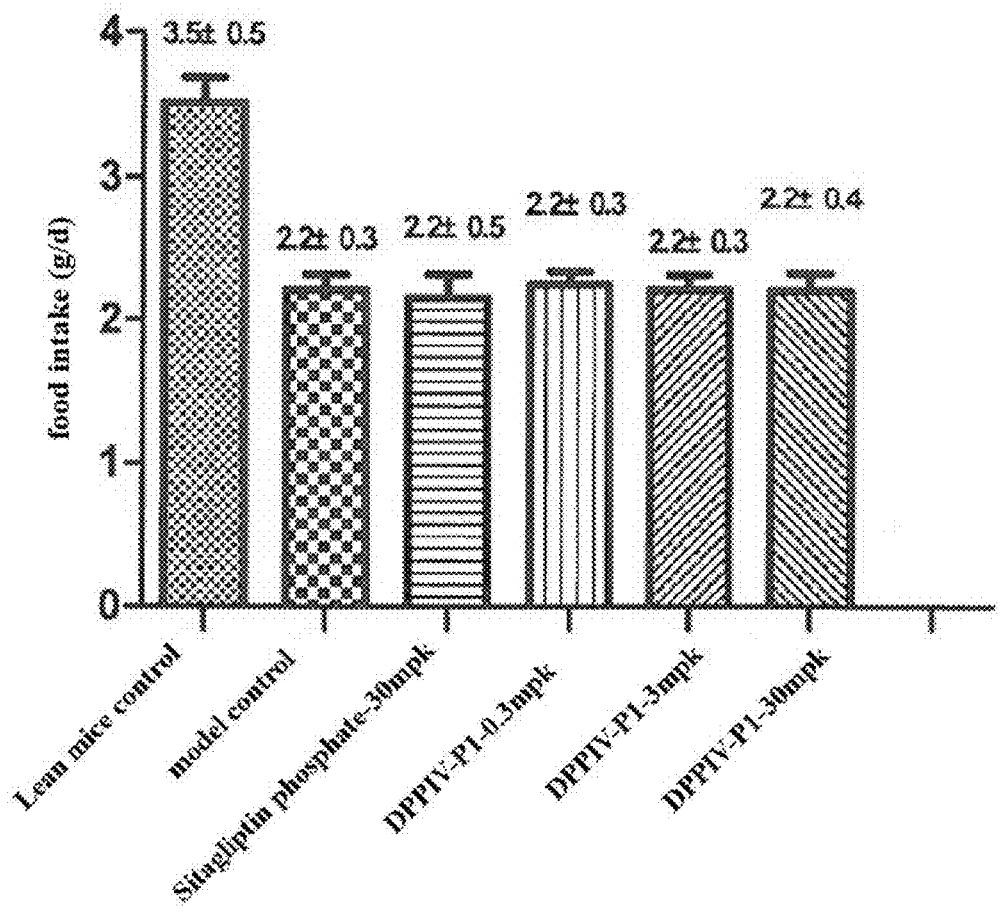
FIG. 37 shows food intake data of each group (mean value±standard deviation, n=1).

The influence of DPPIV-P1 on the weight of the DIO mice was as follows: FIG. 31 and Table 16 showed the results of weight detection during the experiment, and FIG. 32 and Table 17 showed the weight after the drug was administrated for 28 days. There was no significant difference between the weight on the 28th day of drug administration and the weight at the beginning of drug administration.

TABLE 16

| Group and dose (mg/kg) | Weight (g) | | | | |
|---|---|---|---|---|---|
| | D1 | D7 | D14 | D21 | D28 |
| Lean mice control | 29.1 ± 2.1 | 29.2 ± 2.4 | 29.9 ± 2.6 | 30.4 ± 2.7 | 29.7 ± 2.5 |
| Model control | 41.8 ± 3.9 | 40.6 ± 4.1 | 41.0 ± 4.0 | 44.4 ± 3.7 | 46.0 ± 3.4 |
| Sitagliptin phosphate-30 | 37.2 ± 4.4 | 35.3 ± 3.7 | 34.4 ± 4.9 | 37.2 ± 5.3 | 39.5 ± 5.0 |
| DPPIV-P1-0.3 | 38.9 ± 3.8 | 37.4 ± 3.4 | 38.2 ± 4.2 | 40.2 ± 4.2 | 39.5 ± 5.0 |
| DPPIV-P1-3 | 41.5 ± 3.5 | 40.9 ± 4.2 | 43.1 ± 4.9 | 44.2 ± 5.1 | 45.0 ± 5.4 |
| DPPIV-P1-30 | 41.5 ± 3.1 | 40.5 ± 3.0 | 41.2 ± 4.4 | 41.3 ± 3.5 | 42.9 ± 5.6 |

TABLE 17

| Group and dose (mg/kg) | | | | | |
|---|---|---|---|---|---|
| Lean mice control | Model control | Sitagliptin phosphate-30 | DPPIV-P1-0.3 | DPPIV-P1-3 | DPPIV-P1-30 |
| 29.6 | 49.2 | 40.8 | 40.8 | 43.1 | 48.2 |
| 29.6 | 47.0 | 45.6 | 45.6 | 46.4 | 51.8 |
| 30.9 | 43.5 | 47.1 | 47.1 | 39.7 | 48.6 |
| 27.4 | 42.2 | 41.0 | 41.0 | 50.2 | 41.0 |
| 32.7 | 46.6 | 39.9 | 39.9 | 46.8 | 46.6 |
| 32.0 | 46.1 | 39.9 | 39.9 | 42.6 | 36.5 |
| 33.0 | 49.6 | 31.0 | 31.0 | 54.1 | 43.6 |
| 25.0 | 45.2 | 34.8 | 34.8 | 46.8 | 36.8 |
| 28.6 | 41.4 | 41.6 | 41.6 | 48.3 | 36.7 |
| 30.8 | 42.9 | 32.2 | 32.2 | 34.4 | 39.3 |
| 27.0 | 52.3 | 40.5 | 40.5 | 42.2 | 38.7 |

The influence of DPPIV-P1 on related metabolic parameters of the DIO mice was as follows: at the end of the experiment, the mice were fasted overnight (16 h), the blood was sampled and the free fatty acid (NEFA), total cholesterol (TCHO), triglyceride (TG), insulin and DPPIV activity were measured by using serum. FIG. 33, FIG. 34, FIG. 35, FIG. 36 and FIG. 37 showed the data statistics of NEFA, TCHO, TG, insulin, and food intake, respectively. The data showed that, at the end of long-term administration, compared with the model control group, the total cholesterol (TCHO) in the sitagliptin phosphate-30 group and the DPPIV-P1-30 group was decreased by 25.4% (P<0.01) and 18.4% (P<0.01), respectively. The insulin in the sitagliptin phosphate-30 group and the DPPIV-P1-0.3 group was decreased by 58.3% and 28.3% respectively (which has no significant difference in comparison with the model control group), and other metabolic data had no significant difference. Table 18 was a total data table of the metabolic parameters.

TABLE 18

| Parameter (unit) | Group and dose (mg/kg) | | | | | |
|---|---|---|---|---|---|---|
| | Lean mice control | Model control | Sitagliptin phosphate-30 | DPPIV-P1-0.3 | DPPIV-P1-3 | DPPIV-P1-30 |
| Serum NEFA (mmol/L) | 1.29 ± 0.1 | 1.08 ± 0.11 | 1.11 ± 0.13 | 1.21 ± 0.07 | 1.08 ± 0.14 | 1.01 ± 0.11 |
| Serum TCHO (mmol/L) | 2.58 ± 0.34 | 5.35 ± 0.62 | 3.99 ± 0.798** | 5.01 ± 0.58 | 5.06 ± 0.65 | 4.36 ± 0.45** |
| Serum TG (mmol/L) | 0.68 ± 0.08 | 0.97 ± 0.12 | 0.94 ± 0.11 | 1.04 ± 0.13 | 0.94 ± 0.15 | 0.83 ± 0.11 |
| Serum insulin (ng/mL) | 0.7 ± 0.29 | 4.2 ± 2.62 | 2.2 ± 1.38 | 3.2 ± 2.44 | 4.7 ± 3.55 | 4.9 ± 4.04 |
| Food intake (g/d) | 3.5 ± 0.5 | 2.2 ± 0.3 | 2.2 ± 5.0 | 2.2 ± 0.3 | 2.2 ± 0.3 | 2.2 ± 0.4 |
| Weight (g) | 29.7 ± 2.5 | 46.0 ± 3.4 | 39.5 ± 5.0 | 39.5 ± 5.0 | 45.0 ± 5.4 | 42.9 ± 5.6 |

**p < 0.01 vs the model control group

Figure 25:
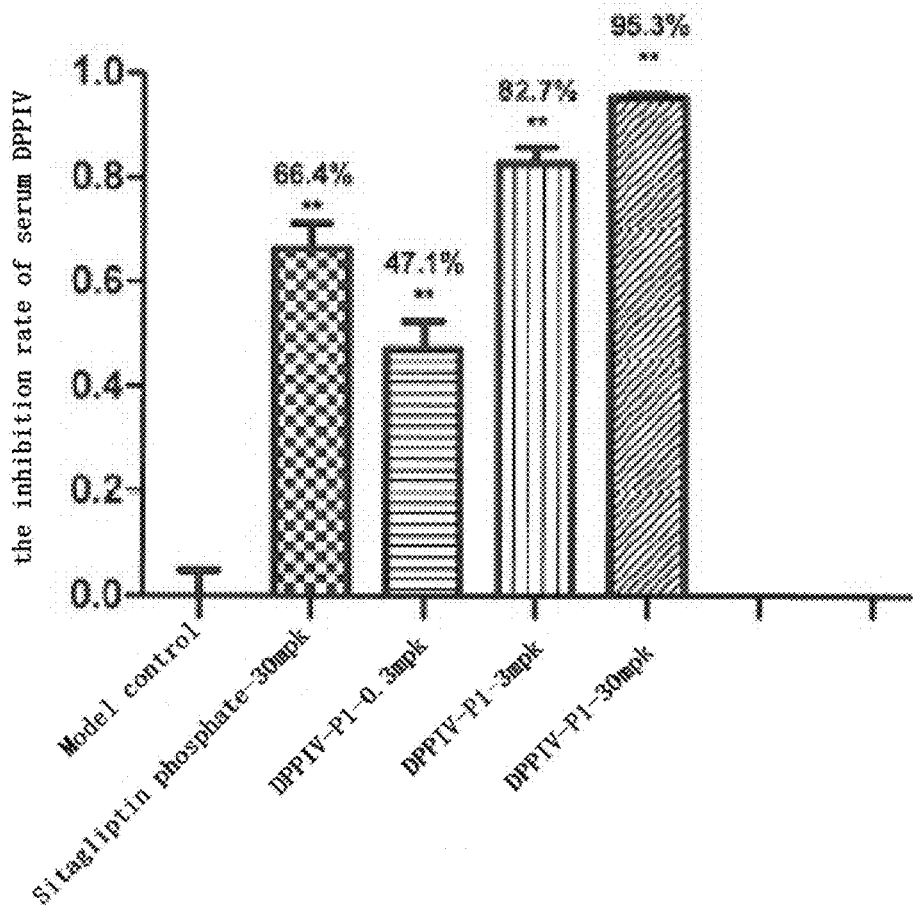
FIG. 25 shows the inhibition rate of serum DPPIV of each group, wherein the inhibition rate is the comparison result with a model control group (mean value±standard deviation, n=11)

The influence of DPPIV-P1 on the DPPIV activity of the DIO mice was as follows: FIG. 25 showed the result of the inhibition effect of the drug against the serum DPPIV in each group; the inhibition effect of DPPIV-P1 against DPPIV was dose-dependent, and, the inhibition rates of the DPPIV-P1-0.3, DPPIV-P1-3 and DPPIV-P1-30 against DPPIV were 47.1%, 82.7% and 95.3% respectively, which were significantly different from that of the model control group (p<0.01). The inhibition rate of the sitagliptin phosphate-30 against DPPIV was 66.4%, and the result was basically consistent with the inhibition rate of blood glucose.

Conclusion: the DIO mice with diet-induced diabetes were administrated with the drug for a long time, and the effect of DPPIV-P1 was observed. The results indicated that the long-term administration of DPPIV-P1 had no obvious effect on the fasting blood glucose of animals, and the results were consistent with the positive drug sitagliptin phosphate, so that it was indicated that the drug was not easy to result in hypoglycemia before the meal.

The long-term oral administration of DPPIV-P1 had no obvious effect on the weight, food intake, serum free fatty acid, triglyceride and other indexes of the animals and did not influence the normal lipid metabolism of the animals. However, both the DPPIV-P1 and the positive drug sitagliptin phosphate could reduce the level of serum insulin, and the degree of reduction was equivalent at different doses of the two drugs. This was related to the insulin secretion insufficiency induced by the lowering of blood glucose by the drugs.

After long-term administration, the inhibition effect of the DPPIV-P1 on the serum DPPIV was obviously higher than that of sitagliptin phosphate, and the inhibition effect of the DPPIV-P1 at the dose of 3 mg/kg was basically equivalent to that of sitagliptin phosphate at the dose of 30 mg/kg.

In conclusion, the DPPIV-P1 was good in tolerance and not easy to induce hypoglycemia after long-term administration. Meanwhile, compared with sitagliptin phosphate, the DPPIV-P1 had higher inhibition effect on the serum DPPIV.

Example 4: Method for Preparing the Phosphate Crystal Form B of the Compound of Formula (I)

15 mg of the amorphous phosphate of the compound of formula (I) prepared in Example 1 was dissolved in isopropyl alcohol to obtain a saturated solution, and the solvent was slowly volatilized at the room temperature (25±2° C.) to obtain solid. After detection, the obtained solid was the crystal form B of phosphate.

Example 5: Method for Preparing the Phosphate Crystal Form B of the Compound of Formula (I)

15 mg of the amorphous phosphate of the compound of formula (I) prepared in Example 1 was dissolved in 0.3 mL of isoamyl alcohol, and the solvent was slowly volatilized at the room temperature (25±2° C.) to obtain solid. After detection, the obtained solid was the crystal form B of phosphate.

Example 6: Method for Preparing the Phosphate Crystal Form B of the Compound of Formula (I)

Figure 13:
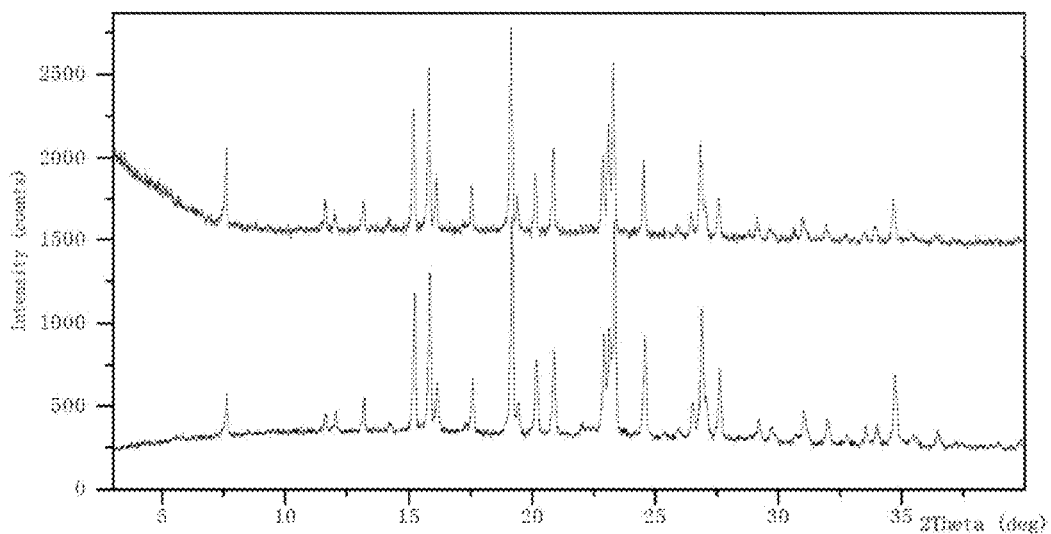
FIG. 13 shows an XRPD pattern of the phosphate crystal form B in Example 6, wherein the upper line shows a sample of Example 6 and the lower line shows a sample of Example 3.

1. 150 mg of the amorphous phosphate prepared in Example 1 was put into a 20 mL glass bottle.
2. 4 mL of a mixed solution of isoamyl alcohol/water (19/1, v/v) was added, stirred and dissolved.
3. 5 mg of the crystal seed of the phosphate crystal form B prepared in Example 3 was added into the glass bottle.
4. The mixture was magnetically stirred (500 rpm) at the room temperature, samples were collected for analysis after 18 h, the XRPD result indicated that the phosphate crystal form B was obtained, and the XRPD pattern was shown in FIG. 13.

Example 7

1. 150 mg of the amorphous phosphate prepared in Example 1 was put into a 20 mL glass bottle.
2. 4 mL of a mixed solution of isopropyl alcohol/methyl tert-butyl ether (1/1, v/v) was added, stirred and dissolved.
3. 5 mg of the crystal seed of the phosphate crystal form B prepared in Example 3 was added into the glass bottle.
4. The solution was slowly volatilized at the room temperature to obtain a single crystal of the phosphate crystal form B.

Figure 14:
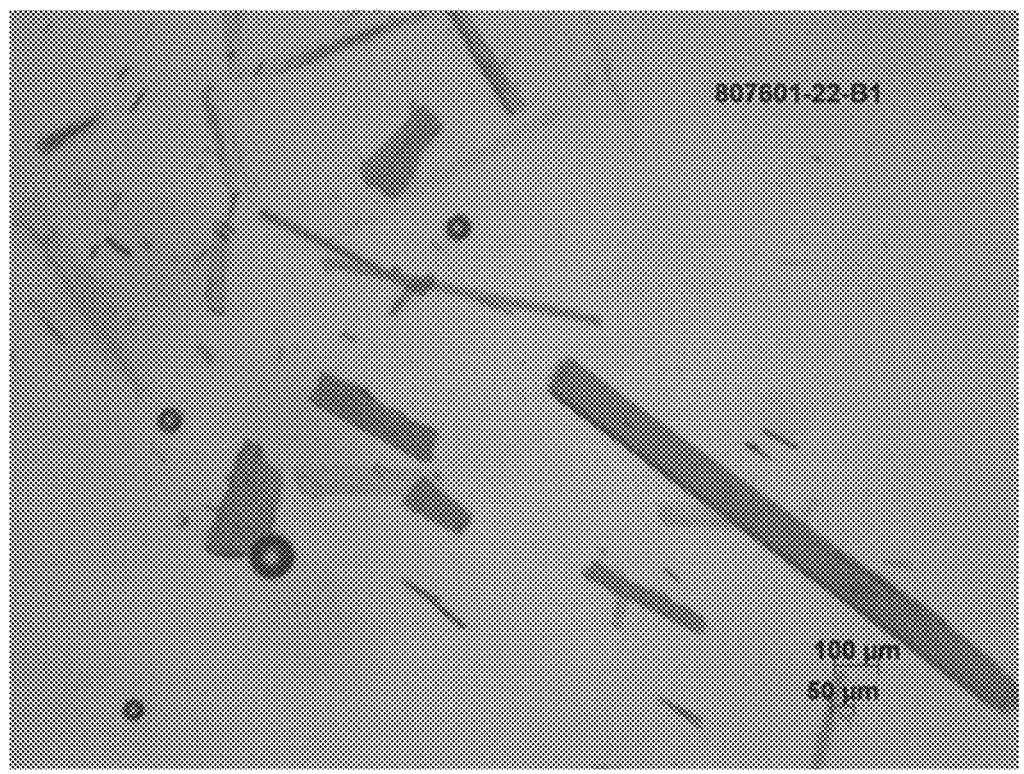
FIG. 14 shows a micrograph of a single crystal of the phosphate crystal form B in Example 7.

FIG. 14 is a microphotograph of the single crystal of the phosphate crystal form B.

Figure 15:
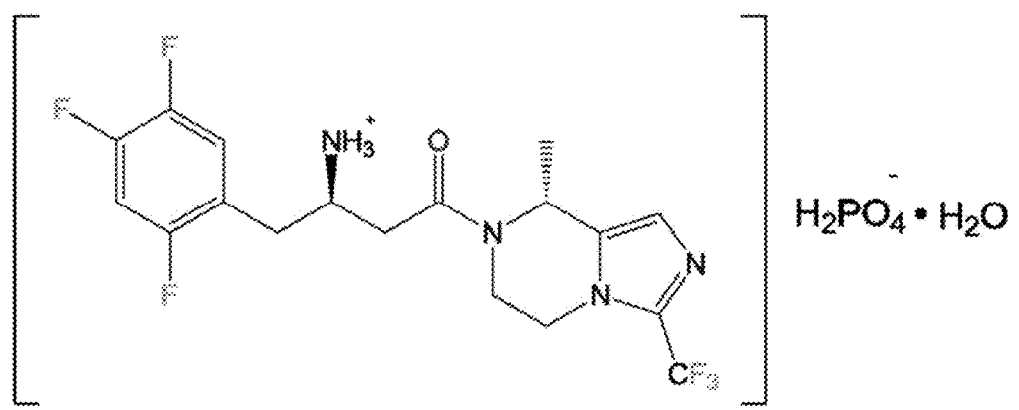
FIG. 15 shows a chemical structure of the phosphate crystal form B.
Figure 16:
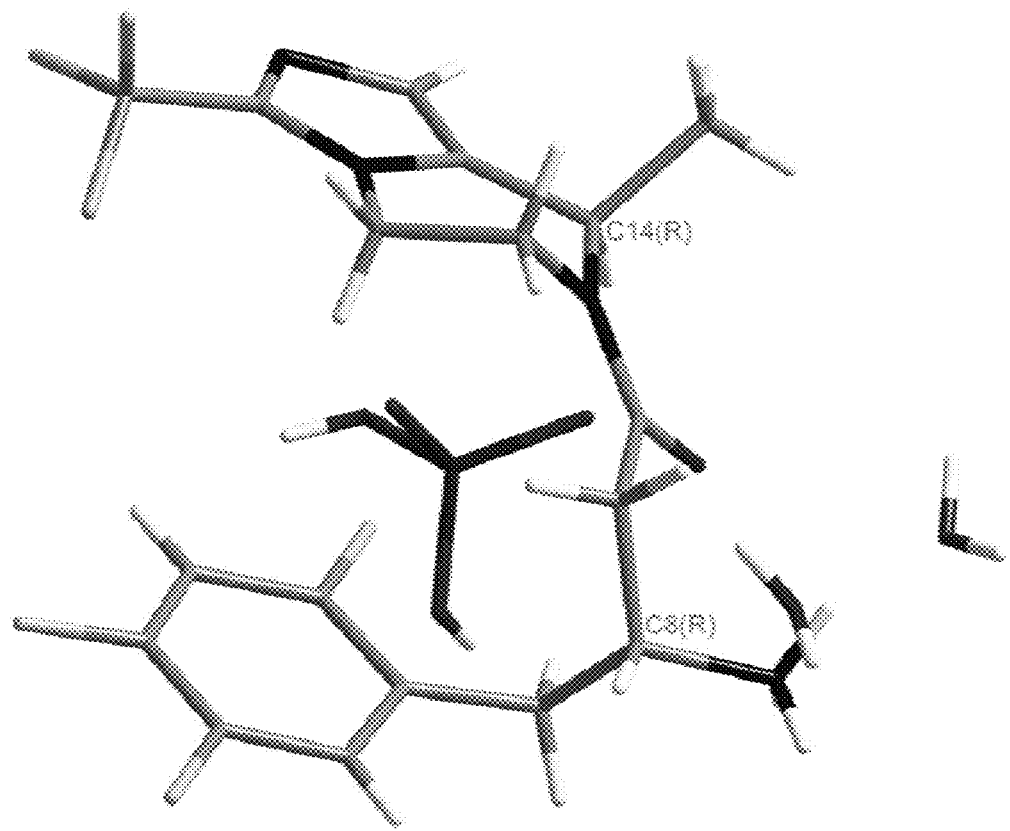
FIG. 16 shows a stereoscopic structure of the crystal form B.
Figure 17:
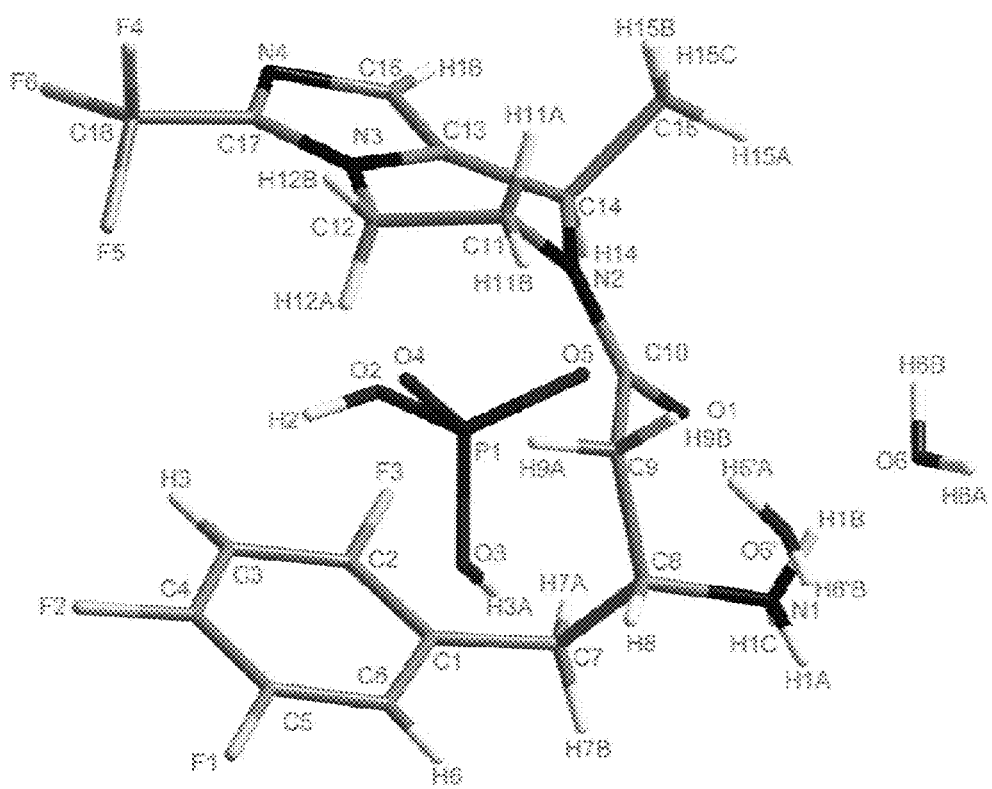
FIG. 17 shows a molecular structure of the crystal form B.
Figure 18:
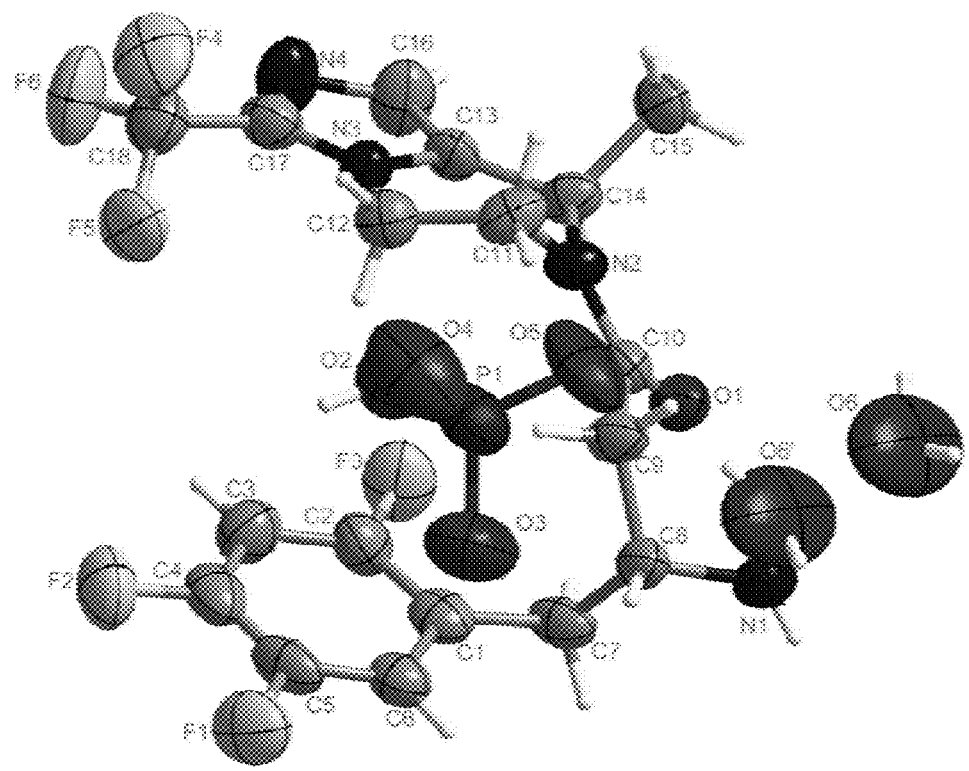
FIG. 18 shows an ellipsoid diagram of the crystal form B.
Figure 19:
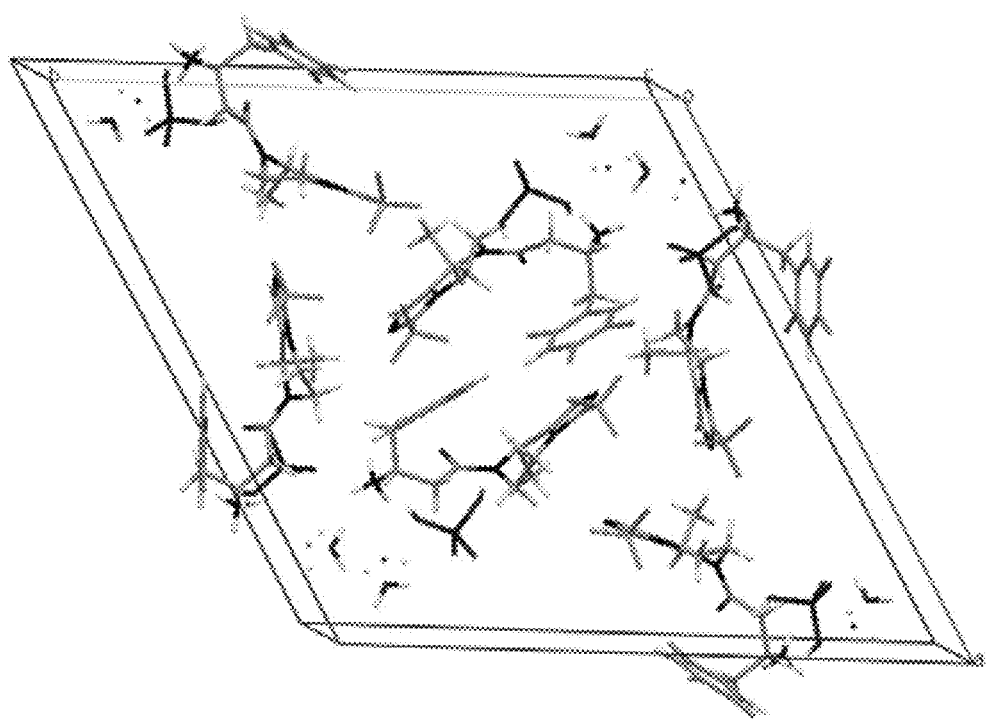
FIG. 19 shows a diagram of a unit cell of a single crystal of the crystal form B.
Figure 20:
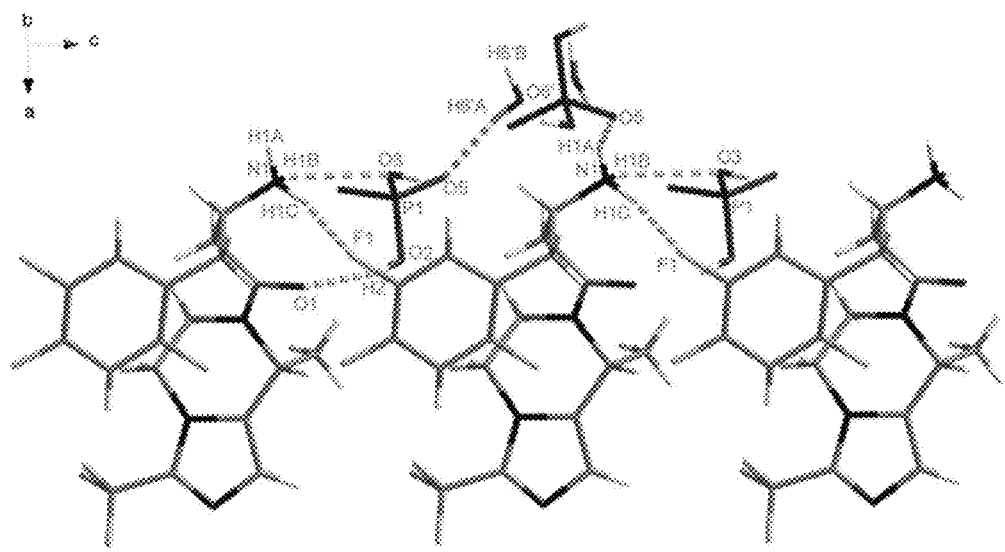
FIG. 20 shows a schematic diagram of a hydrogen bond in the single crystal of the crystal form B.
Figure 21:
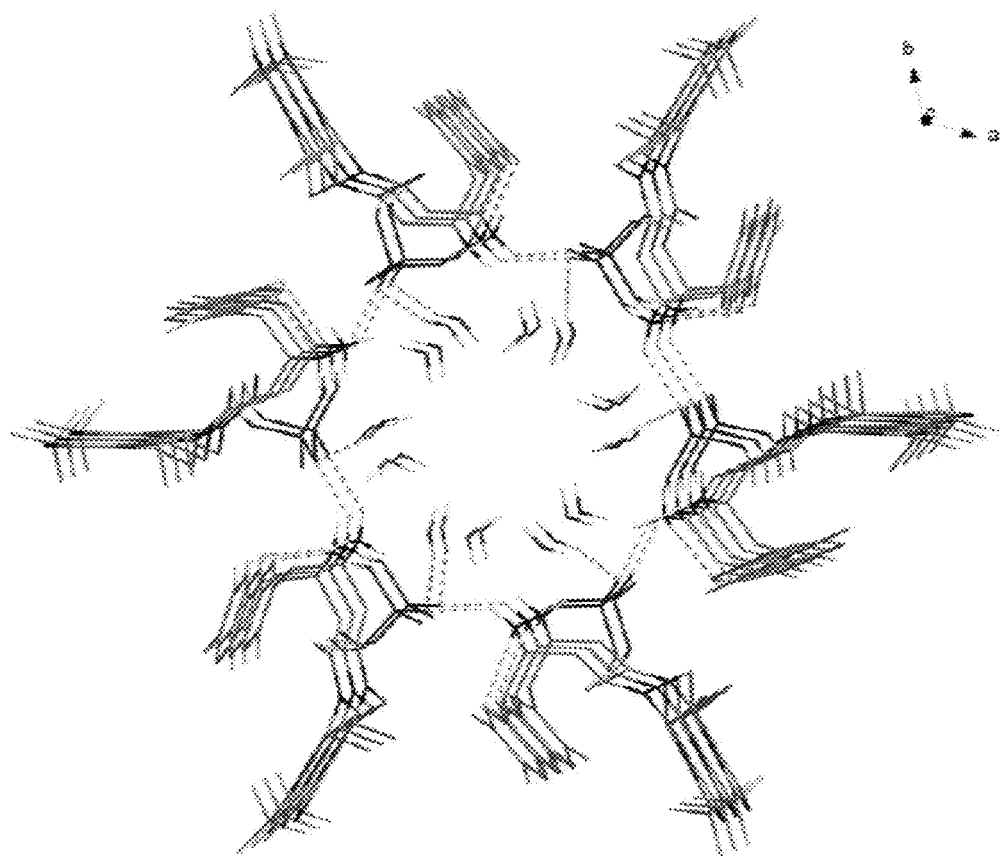
FIG. 21 shows a one-dimensional chain structure of the single crystal of the crystal form B.
Figure 22:
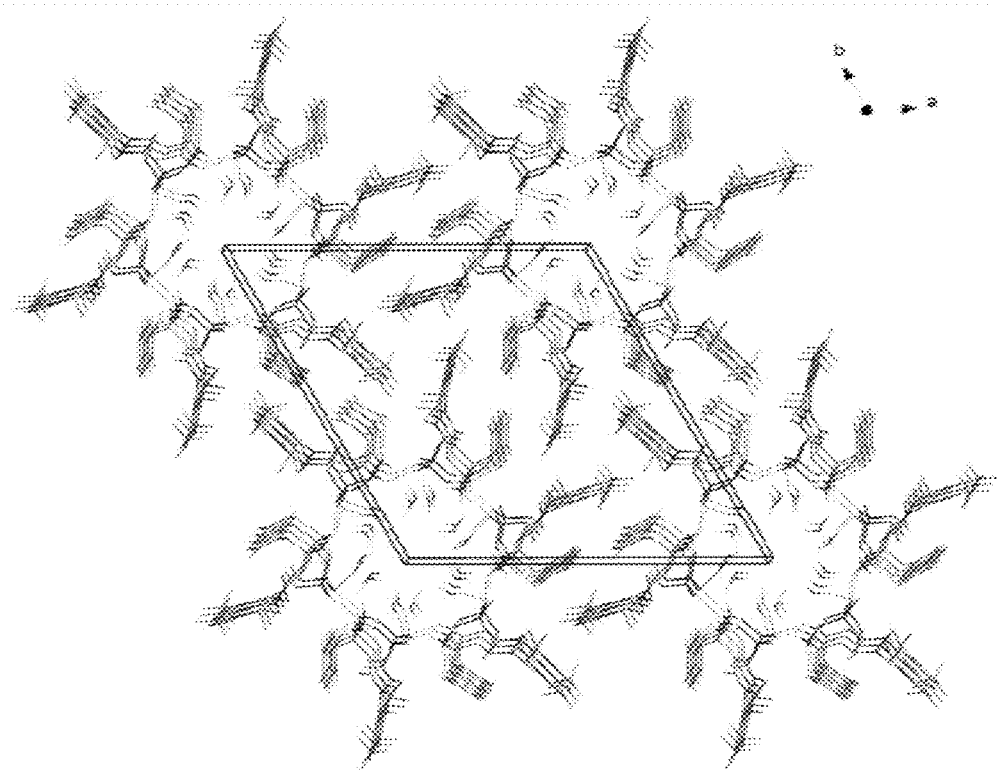
FIG. 22 shows a stack diagram of single crystals of the crystal form B.
Figure 23:
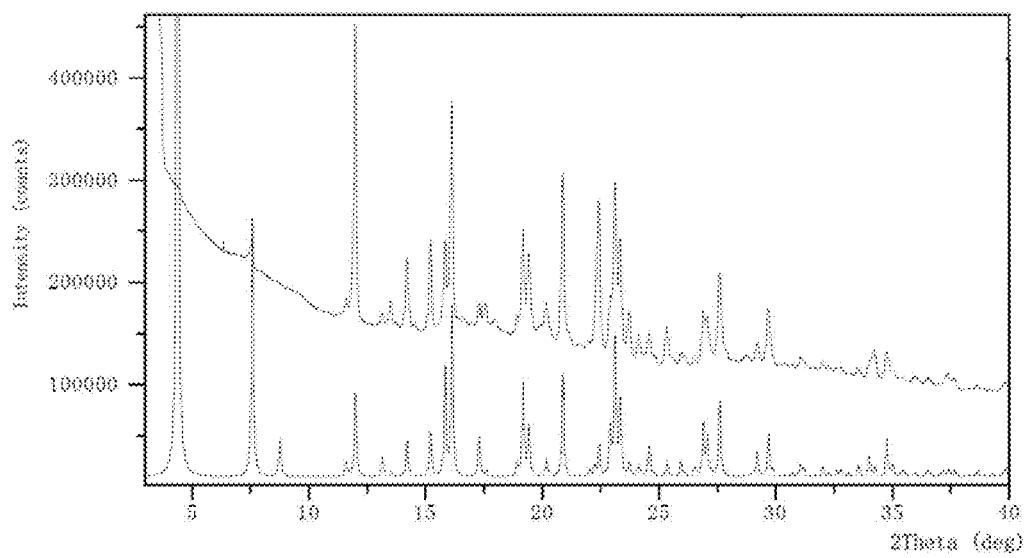
FIG. 23 shows a comparison diagram between the simulated XRPD of the single crystal structure of the crystal form B and the transmission XRPD of the crystal form B prepared in Example 7, wherein the upper line shows the crystal form B and the lower line shows the simulated XRPD.
Figure 24:
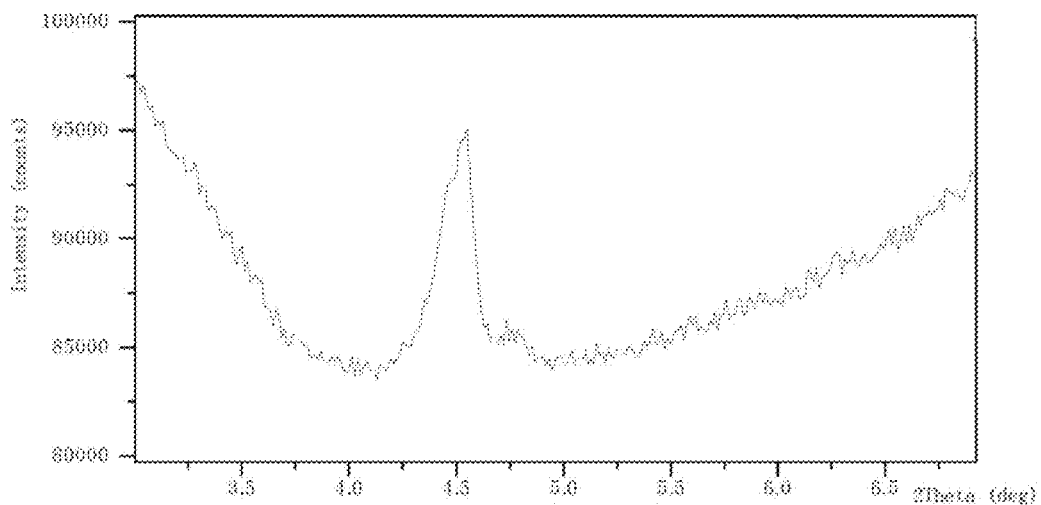
FIG. 24 shows a 3-hour scan of reflected XRPD at 3° to 7°.

Needle-like single crystals of the phosphate crystal form B were selected, diffraction data of the single crystals was acquired, and the single crystal structure was successfully analyzed. The following Table 19 showed the single crystal structure and the structure correction data. FIG. 15 was a chemical structure of the crystal form B. FIG. 16, FIG. 17 and FIG. 18 showed a stereoscopic structure diagram, a molecular structure diagram and an ellipsoid diagram of the crystal form B, respectively. The chemical structure of the crystal form B was determined by the single crystal structure analysis, and the molar ratio of free base to phosphate radial to water molecule in the structure was 1:1:1. The single crystal structure also confirmed the absolute configuration of chiral carbon atoms C8(R) and C14(R) of the crystal form B. In the structure of the crystal form B, O6 and O6' were disorders of the same water molecule. Due to the large thermal vibration of this water molecule, the probability of occurrence at the site of O6 and O6' was 50%, respectively. FIG. 19 was a diagram of a unit cell of the single crystal of crystal form B. In the basic structure unit of the crystal, there were totally 6 basic units of the crystal form B, i.e., 6 free bases, 6 phosphate radicals and 6 water molecules. FIG. 20 was a schematic diagram of a hydrogen bond in a single crystal of the crystal form B. In the structure of the crystal form B, the amino group in each free base was connected with two adjacent free bases by an N—H . . . F hydrogen bond, and extended in the c-axis direction to form a one-dimensional chain structure. These one-dimensional chains were linked by phosphate radicals bond through N—H . . . O hydrogen bonds to form a one-dimensional hole structure in the c-axis direction, and water molecules were bonded with the phosphate radicals through O—H . . . O hydrogen bonds and filled in the one-dimensional hole formed by the free bases and the phosphate radicals, as shown in FIG. 21. FIG. 22 was a stack diagram of single crystals of the crystal form B. FIG. 23 was a comparison diagram between the simulated XRPD according to the single crystal structure of the crystal form B and the transmission XRPD of the crystal form B prepared in Example 7. It could be known from the comparison diagram that the simulated XRPD of the single crystal structure is basically the same as the XRPD of the crystal form B. In the transmission diagram, the diffraction peak at the position of 2Theta of 4.38 degrees was not as obvious as that in the simulated XRPD (FIG. 24 was a 3-hour scan of the reflected XRPD at 3°-7°, and the diffraction peak could be seen). This may be caused by preferred orientation.

The micrograph of the single crystal sample was shot at the room temperature by Shanghai dimension measurement stereomicroscope PXS9-T. The diffraction data of the single crystals were acquired by Bruker D8 ADVANCE single crystal diffractometer (Mo Kα, λ=0.71073 Å) at 290(2) K. The crystal structure was solved by a direct method (SHELXTL and OLEX2), coordinates of all non-hydrogen atoms were then determined by several rounds of difference Fourier synthesis, and the anisotropic temperature factors of all the non-hydrogen atoms were corrected by a full-matrix least square method. The structure diagram was generated by Diamond, and the unit cell diagram and the theoretically simulated XRPD pattern were generated by Mercury. The transmission XRPD data was acquired by the PANalytical Empyrean X-ray powder diffractometer. The reflected XRPD data was acquired by the Xpert 3 X-ray powder diffractometer.

TABLE 19

| | | |
|---|---|---|
| Temperature | 290(2) K | — |
| wavelength | 0.71073 Å | — |
| crystal system, space group | Hexagonal | P63 |
| | a = 23.2572(5) Å | α = 90 deg. |
| Unit cell parameter | b = 23.2572(5) Å | β = 90 deg. |
| | c = 7.9137(4) Å | γ = 120 deg. |
| Volume | 3707.0(2) Å 3 | — |
| Z value, theoretically calculated density | 6 | 1.442 Mg/m³ |
| Absorption coefficient | 0.196 mm⁻¹ | — |
| the number of electrons in the unit cell | 1656 | — |
| crystal size | 0.23 × 0.12 × 0.10 mm³ | — |
| the range of data acquisition angle | 1.01-27.50 deg. | — |
| maximum and minimum diffraction indexes | −30 ≤ h ≤ 28, −30 ≤ k ≤ 26 −10 ≤ l ≤ 10 | — |
| the number of collected diffraction points/independent diffraction points | 40419/5634 [R(int) = 0.1378] | — |
| integrity | 99.3% | — |
| refinement method | Full-matrix least-squares on F2 | — |
| the number of diffraction points participating in refinement/the number of geometric constraint parameters/the number of participation parameters | 5634/4/320 | — |
| Goof value based on F2 | 1.062 | — |
| R value for observable diffraction points | R1 = 0.0960 | wR2 = 0.2399 |
| Flack parameters | 0.0(4) | — |
| Maximum residual electron density | 0.989 and −0.468 e · Å−3 | — |

Comparative Example 4

15 mg of the amorphous phosphate of the compound of formula (I) prepared in Example 1 was put into a 1.5 mL small bottle, 0.2 to 0.5 mL of each of the solvents shown in the following table was added in the small bottle respectively to obtain a suspension solution, the suspension solution was magnetically stirred for 3 days at the room temperature, and the solid was separated by centrifugation and subjected to the XRPD test. The results were shown in Table 20 below, wherein N/A indicated that no solid was obtained. In addition, in the present disclosure, a suspension stirring experiment was carried out at 5° C. and 50° C., but no crystal form was obtained.

TABLE 20

| Test No. | Solvent used (v/v) | Obtained crystal form |
|---|---|---|
| Comparative example 4-1 | EtOAc | N/A |
| Comparative example 4-2 | IPAc | Amorphous |
| Comparative example 4-3 | MTBE | Amorphous |
| Comparative example 4-4 | MIBK | Amorphous |
| Comparative example 4-5 | CHCl3 | N/A |
| Comparative example 4-6 | DCM | N/A |
| Comparative example 4-7 | Toluene | Amorphous |
| Comparative example 4-8 | Heptane | Amorphous |
| Comparative example 4-9 | 1,4-Dioxane | N/A |
| Comparative example 4-10 | MeOH/MTBE (1/5) | N/A |
| Comparative example 4-11 | EtOH/IPAc (1/5) | |
| Comparative example 4-12 | IPA/Toluene (1/5) | N/A |
| Comparative example 4-13 | THF/Heptane (1/5) | Amorphous |
| Comparative example 4-14 | Acetone/EtOAc (1/3) | N/A |
| Comparative example 4-15 | ACN/EtOAc (1/3 ) | N/A |
| Comparative example 4-16 | MeOH/DCM (1/5) | N/A |
| Comparative example 4-17 | MeOH/1,4-Dioxane (1/5) | N/A |
| Comparative example 4-18 | IAA | N/A |

Comparative Example 5

15 mg of the amorphous phosphate of the compound of formula (I) prepared in Example 1 was dissolved in MeOH, IPAc, ACN, Acetone, 2-Butanone, THF, 2-MeTHF, 1,4-Dioxane, H₂O, Acetic acid, MeOH/EtOAc(1/1), Acetone/IPAc(1/1), Acetone/DCM(1/1), EtOH/CHCl₃(1/1), IPA/Heptane(1/1), THF/Toluene(1/1), MeOH/CHCl₃(5/1) and MeOH/Heptane(5/1) respectively to obtain clear solutions, the solutions were slowly volatilized at the room temperature (25±2° C.), and no solid was obtained.

Comparative Example 6

15 mg of the amorphous phosphate of the compound of formula (I) prepared in Example 1 was dissolved in MeOH, EtOH, IPAc, ACN, Acetone, 2-Butanone, THF, 2-MeTHF, 1,4-Dioxane, H$_2$O, Acetic acid, MeOH/EtOAc(1/1), Acetone/IPAc(1/1), Acetone/DCM(1/1), EtOH/CHCl$_3$(1/1), IPA/Heptane(1/1). THF/Toluene(1/1), MeOH/CHCl$_3$(5/1) and MeOH/Heptane(5/1) respectively to obtain clear solutions, the solutions were slowly volatilized at the room temperature or 5° C., and no solid was obtained.

Comparative Example 7

15 mg of the amorphous phosphate of the compound of formula (I) prepared in Example 1 was put into a 3 mL small bottle, the good solvents shown in the following table were added in the small bottle to obtain a clear solution, the opened glass bottle was placed in a 20 mL glass bottle containing 4 mL of the corresponding anti-solvent (see Table 21 below), and the glass bottle was sealed and placed for 5 days at the room temperature. The results were shown in Table 21 below, and no solid was obtained.

TABLE 21

| Test No. | Good solvent | Anti-solvent | Obtained crystal form |
|---|---|---|---|
| Comparative example 7-1 | EtOH | Hexane | N/A |
| Comparative example 7-2 | IPA | IPAc | N/A |
| Comparative example 7-3 | 2-MeTHF | Heptane | N/A |
| Comparative example 7-4 | NMP | Heptane | N/A |
| Comparative example 7-5 | THF | EtOAc | N/A |
| Comparative example 7-6 | 1,4-Dioxane | EtOAc | N/A |
| Comparative example 7-7 | DMSO | EtOAc | N/A |
| Comparative example 7-8 | DMF | DCM | N/A |
| Comparative example 7-9 | ACN | DCM | N/A |
| Comparative example 7-10 | 2-Buranone | DCM | N/A |
| Comparative example 7-11 | 2-MeTHF | DCM | N/A |
| Comparative example 7-12 | 2-MeTHF | 1,4-Dioxane | N/A |
| Comparative example 7-13 | NMP | EtOAc | N/A |
| Comparative example 7-14 | NMP | 1,4-Dioxane | N/A |
| Comparative example 7-15 | NMP | DCM | N/A |
| Comparative example 7-16 | IPA | MTBE | N/A |
| Comparative example 7-17 | IPA | Heptane | N/A |
| Comparative example 7-18 | 2-MeTHF | EtOAc | N/A |
| Comparative example 7-19 | 2-MeTHF | IPAc | N/A |
| Comparative example 7-20 | 2-MeTHE | MTBE | N/A |
| Comparative example 7-21 | 2-MeTHF | Toluene | N/A |
| Comparative example 7-22 | EtOH | EtOAc | N/A |
| Comparative example 7-23 | EtOH | IPAc | N/A |
| Comparative example 7-24 | EtOH | MTBE | N/A |
| Comparative example 7-25 | EtOH | DCM | N/A |
| Comparative example 7-26 | ACN | EtOAc | N/A |
| Comparative example 7-27 | ACN | IPAc | N/A |
| Comparative example 7-28 | ACN | MTBE | N/A |
| Comparative example 7-29 | ACN | Toluene | N/A |
| Comparative example 7-30 | MEK | EtOAc | N/A |
| Comparative example 7-31 | MEK | IPAc | N/A |
| Comparative example 7-32 | MEK | MTBE | N/A |
| Comparative example 7-33 | MEK | DCM | N/A |
| Comparative example 7-34 | MEK | Toluene | N/A |
| Comparative example 7-35 | MEK | Heptane | N/A |

In the present disclosure, gas-solid permeation tests of various solvents, an anti-solvent addition test, an anti-antisolvent addition test, a slow cooling test, a polymer induction test, an ionic liquid induction test, a wet grinding test and a slow precipitation test were also carried out, and no crystal form was obtained.

Example 8: Method for Preparing Amorphous Oxalate of the Compound of Formula (I)

20 mg of the compound of formula (I) was dissolved in 0.5 mL of methyl tert-butyl ether and then added with oxalic acid of the same molar amount as the compound of formula (I); the mixture was stirred and reacted for 12 h at the room temperature (25±2° C.), and a solid was obtained. After detection, the obtained solid was an amorphous form of oxalate.

Example 9: Method for Preparing an Oxalate Crystal Form A of the Compound of Formula (I)

20 mg of the compound of formula (I) was dissolved in 0.5 mL of methanol and then added with oxalic acid of the same molar amount as the compound of formula (I); the mixture was stirred and reacted for 12 h at the room temperature (25±2° C.), and a solid was obtained.

Figure 26:
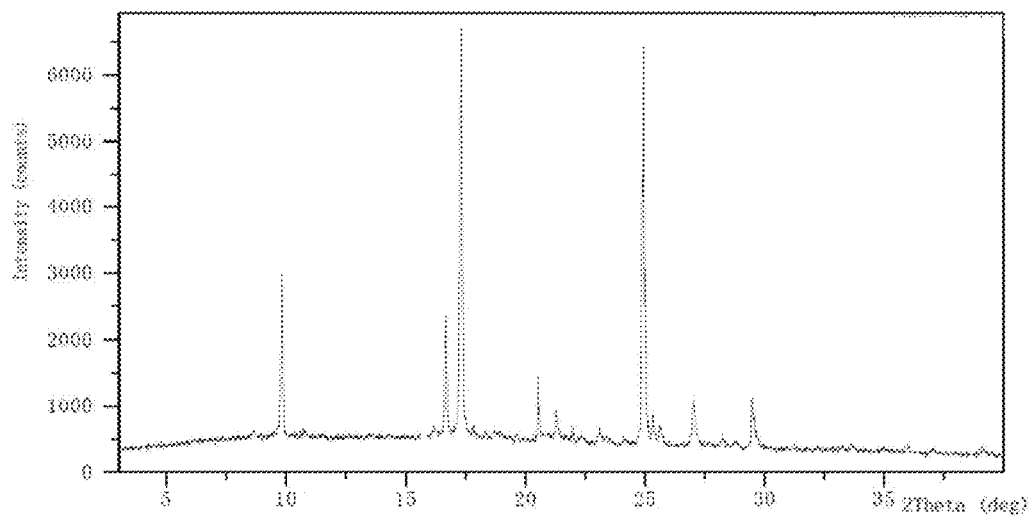
FIG. 26 shows an XRPD pattern of an oxalate crystal form A in Example 9.
Figure 27:
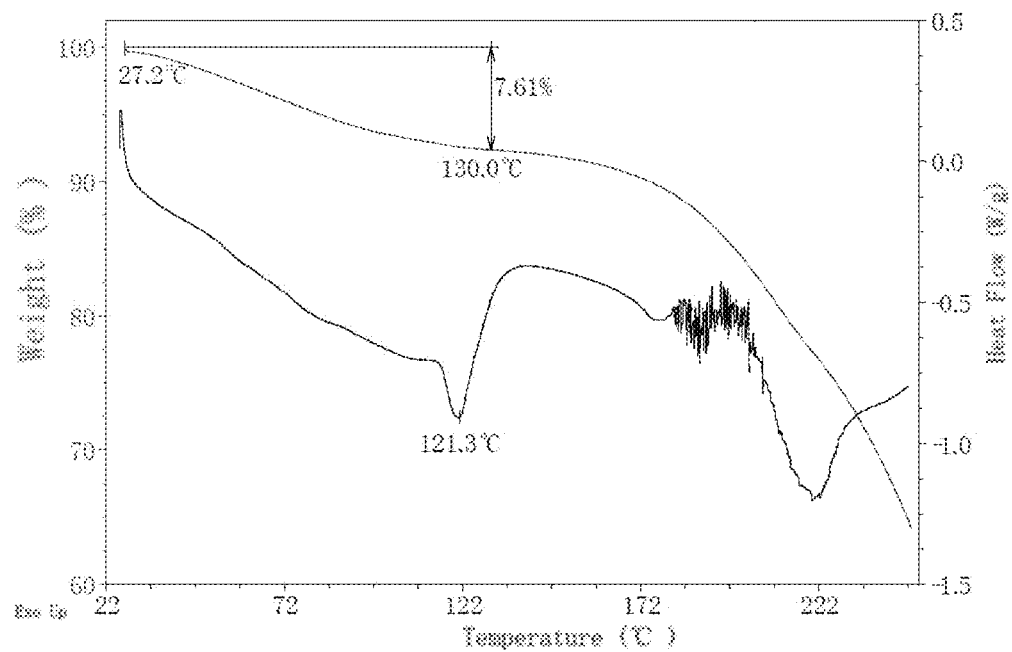
FIG. 27 shows a TGA chart and a DSC chart of the oxalate crystal form A in Example 9.

After detection, the obtained solid was the crystal form A of oxalate, its X-ray powder diffraction data was shown in Table 22 below, its XRPD pattern was shown in FIG. 26, its TGA chart and DSC chart were shown in FIG. 27. The XRPD pattern indicated a high crystallinity, the TGA result indicated that the sample had a weight loss of 7.6% when heated to 130° C., and the DSC result indicated that the sample had an endothermic peaks of 121.3° C. (peak temperature) before decomposition.

TABLE 22

| Pos. [°2Th.] | Height [cts] | FWHM Left [°2Th.] | d-spacing [Å] | Rel. Int. [%] |
|---|---|---|---|---|
| 8.634665 | 114.098100 | 0.153504 | 10.24088 | 1.87 |
| 9.815229 | 2462.449000 | 0.051168 | 9.01161 | 40.38 |
| 10.774090 | 112.768600 | 0.204672 | 8.21166 | 1.85 |
| 16.663470 | 1654.128000 | 0.076752 | 5.32032 | 27.13 |
| 17.306330 | 6097.554000 | 0.076752 | 5.12411 | 100.00 |
| 17.816460 | 156.960100 | 0.102336 | 4.97853 | 2.57 |
| 18.334490 | 129.428700 | 0.076752 | 4.83902 | 2.12 |
| 20.543480 | 628.479500 | 0.076752 | 4.32341 | 10.31 |
| 21.263650 | 432.538800 | 0.063960 | 4.17858 | 7.09 |
| 21.979220 | 151.232600 | 0.076752 | 4.04413 | 2.48 |
| 23.093270 | 191.392500 | 0.102336 | 3.85150 | 3.14 |
| 24.915700 | 4651.254000 | 0.102336 | 3.57376 | 76.28 |
| 25.340420 | 400.914200 | 0.102336 | 3.51482 | 6.58 |
| 25.640500 | 274.723400 | 0.127920 | 3.47436 | 4.51 |
| 27.011890 | 688.676800 | 0.063960 | 3.30100 | 11.29 |
| 28.226050 | 177.515900 | 0.076752 | 3.16171 | 2.91 |
| 29.467570 | 748.330000 | 0.051168 | 3.03127 | 12.27 |

Comparative Example 8

20 mg of the compound of formula (I) was dissolved in 0.5 mL of methyl ten-butyl ether and then added with nicotinic acid of the same molar amount as the compound of formula (I); the mixture was stirred and reacted for 12 h at the room temperature (25±2° C.), and no solid was obtained; and, the solvent was continuously volatilized at the room temperature, and no solid was yet obtained.

Comparative Example 9

20 mg of the compound of formula (I) was dissolved in 0.5 mL of methanol and then added with nicotinic acid of the same molar amount as the compound of formula (I); the mixture was stirred and reacted for 12 h at the room temperature (25±2° C.), and no solid was obtained, and, the solvent was continuously volatilized at the room temperature, and no solid was yet obtained.

The foregoing examples are merely for describing the technical concepts and features of the present invention in order to make those skilled in the art understand the contents of the present invention and hereby implement the present invention. However, these examples are not intended to limit the protection scope of the present invention.

The invention claimed is:
1. A salt of a compound of formula (I),

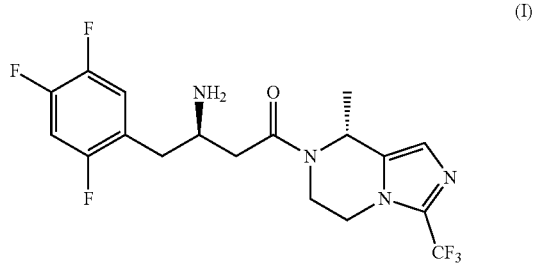 [SMILES: C[C@@H]1c2cnc(C(F)(F)F)n2CCN1C(=O)C[C@H](N)Cc1cc(F)c(F)cc1F]

wherein the salt is crystalline phosphate;
the salt is in a form of crystal form B, and its X-ray powder diffraction pattern has characteristic peaks at positions of which 2theta value is 15.2°±0.2°, 15.9°±0.2°, 19.2°±0.2° and 23.3°±0.2°.

2. The salt of the compound of formula (I) according to claim 1, wherein the X-ray powder diffraction pattern of the crystal form B of the phosphate also has characteristic peaks at positions of which 2theta value is 22.9°±0.2°, 23.1°±0.2° and 26.9°±0.2°.

3. The salt of the compound of formula (I) according to claim 2, wherein the X-ray powder diffraction pattern of the crystal form B of the phosphate also has characteristic peaks at positions of which 2theta value is 20.2°±0.2°, 20.9°±0.2° and 24.6°±0.2°.

4. The salt of the compound of formula (I) according to claim 3, wherein the X-ray powder diffraction pattern of the crystal form B of the phosphate is substantially the same as FIG. 7.

5. The salt of the compound of formula (I) according to claim 1, wherein the crystal form B of the phosphate is monohydrate.

6. A method for preparing the salt of the compound of formula (I) according to claim 1, wherein
a method for preparing the crystal form B of the phosphate is as follows: dissolving the amorphous phosphate of the compound of formula (I) in ethanol, isopropyl alcohol or isoamyl alcohol, and performing solvent evaporation to obtain the crystal form B of the phosphate; or, dissolving the amorphous phosphate of the compound of formula (I) in a mixed solvent of isoamyl alcohol and water or a mixed solvent of isopropyl alcohol and methyl tert-butyl ether, and adding a crystal seed of a crystal form B for induced crystallization to obtain the crystal form B of the phosphate.

7. The preparation method according to claim 6, wherein the volume ratio of the isoamyl alcohol to the water in the mixed solvent used during the preparation of the crystal form B of the phosphate is 18-20:1; the volume ratio of the isopropyl alcohol to the methyl tert-butyl ether in the mixed solvent is 0.8-1.2:1.

8. The preparation method according to claim 6, wherein during the preparation of the crystal form B of the phosphate, the solvent evaporation is performed at 20° C. to 30° C.

9. A pharmaceutical composition, comprising an active component and a pharmaceutically acceptable carrier, wherein the active component is the salt of the compound of formula (I) according to claim 1.

10. An active medicament of dipeptidyl peptidase inhibitor, wherein the dipeptidyl peptidase inhibitor comprises the salt of the compound of formula (I) according to claim 1.

11. A method for treating, controlling or preventing diabetes of mammals, comprising a step of administering an effective dosage of the salt of the compound of formula (I) according to claim 1 to a subject in need of treating, controlling or preventing diabetes.

12. The active medicament of dipeptidyl peptidase inhibitor according to claim 10, wherein the dipeptidyl peptidase inhibitor is the salt of the compound of formula (I) according to claim 1.

* * * * *